United States Patent
Sato

(10) Patent No.: US 6,743,637 B2
(45) Date of Patent: Jun. 1, 2004

(54) DISEASE TYPE AND/OR CONDITION DETERMINATION METHOD AND APPARATUS AND DRUG SCREENING METHOD AND APPARATUS

(76) Inventor: Tomoya Sato, 115-32, Aza Okihara, Oaza Usuichi, Nakasatomachi, Kitatsugaru-gun, Aomori 037-0302 (JP)

(*) Notice: Subject to any disclaimer, the term of this patent is extended or adjusted under 35 U.S.C. 154(b) by 0 days.

(21) Appl. No.: 09/986,613

(22) Filed: Nov. 9, 2001

(65) Prior Publication Data

US 2002/0064882 A1 May 30, 2002

Related U.S. Application Data

(63) Continuation of application No. PCT/JP00/01552, filed on Mar. 14, 2000.

(30) Foreign Application Priority Data

May 10, 1999  (JP) .............................................. 11-128543

(51) Int. Cl.⁷ .............................................. G01N 21/62
(52) U.S. Cl. ........................ 436/171; 436/164; 436/63; 422/82.05; 422/82.09; 356/51; 356/432; 356/436; 356/441
(58) Field of Search ........................ 436/63, 164, 171; 422/82.05, 82.09; 356/51, 300, 432, 436, 441; 435/5, 34, 40.5

(56) References Cited

U.S. PATENT DOCUMENTS

| | | | |
|---|---|---|---|
| 5,038,039 A | * 8/1991 | Wong et al. ............ | 250/339.12 |
| 5,124,932 A | 6/1992 | Lodder ...................... | 702/30 |
| 5,168,162 A | * 12/1992 | Oong et al. ............. | 250/339.12 |
| 5,197,470 A | * 3/1993 | Helfer et al. ................ | 600/342 |
| 5,504,332 A | 4/1996 | Richmond et al. ..... | 250/339.12 |
| 5,539,207 A | * 7/1996 | Wong .................... | 250/339.08 |
| 5,596,992 A | * 1/1997 | Haaland et al. ............ | 600/473 |
| 5,733,739 A | * 3/1998 | Zakim et al. ................. | 435/29 |
| 5,891,619 A | 4/1999 | Zakim et al. ................... | 435/4 |
| 5,976,885 A | * 11/1999 | Cohenford et al. ........... | 436/63 |
| 6,031,232 A | * 2/2000 | Cohenford et al. .... | 250/339.09 |
| 6,146,897 A | * 11/2000 | Cohenford et al. ........... | 436/63 |
| 6,274,871 B1 | * 8/2001 | Dukor et al. .......... | 250/339.12 |
| 6,385,484 B2 | * 5/2002 | Nordstrom et al. ......... | 600/476 |

FOREIGN PATENT DOCUMENTS

| | | | |
|---|---|---|---|
| GB | 1074235 | 7/1967 | .......... C07G/11/00 |
| JP | 9-285286 | 11/1997 | |
| JP | 9-285296 | 11/1997 | |
| JP | 9-286739 | 11/1997 | |
| JP | 9-286740 | 11/1997 | |
| JP | 11-502935 | 3/1999 | |
| WO | WO 96/00892 | 1/1996 | .......... G01N/21/35 |
| WO | PCT/US96/18116 | 5/1997 | |

OTHER PUBLICATIONS

European Search Report for Application No. 00908072.2–2204–JP0001552, mailed Feb. 21, 2003.

* cited by examiner

*Primary Examiner*—Maureen M. Wallenhorst
(74) *Attorney, Agent, or Firm*—Finnegan, Henderson, Farabow, Garrett & Dunner, L.L.P.

(57) ABSTRACT

The object of the present invention is to provide a disease type and/or condition determination method and apparatus that enables rapid and reliable determination by spectral analysis of the energy state of cells or drugs, and a drug screening method and apparatus that enables efficient screening of a target drug. In order to achieve this object, for example, the disease type and/or condition determination method according to the present invention determines disease type and condition by measuring the absorption spectrum in, for example, the infrared region for cells obtained from a specimen, and determining whether or not a coinciding absorption spectrum exists for those measurement results by using as indices at least two infrared absorption spectra.

48 Claims, 32 Drawing Sheets

Fig. 2
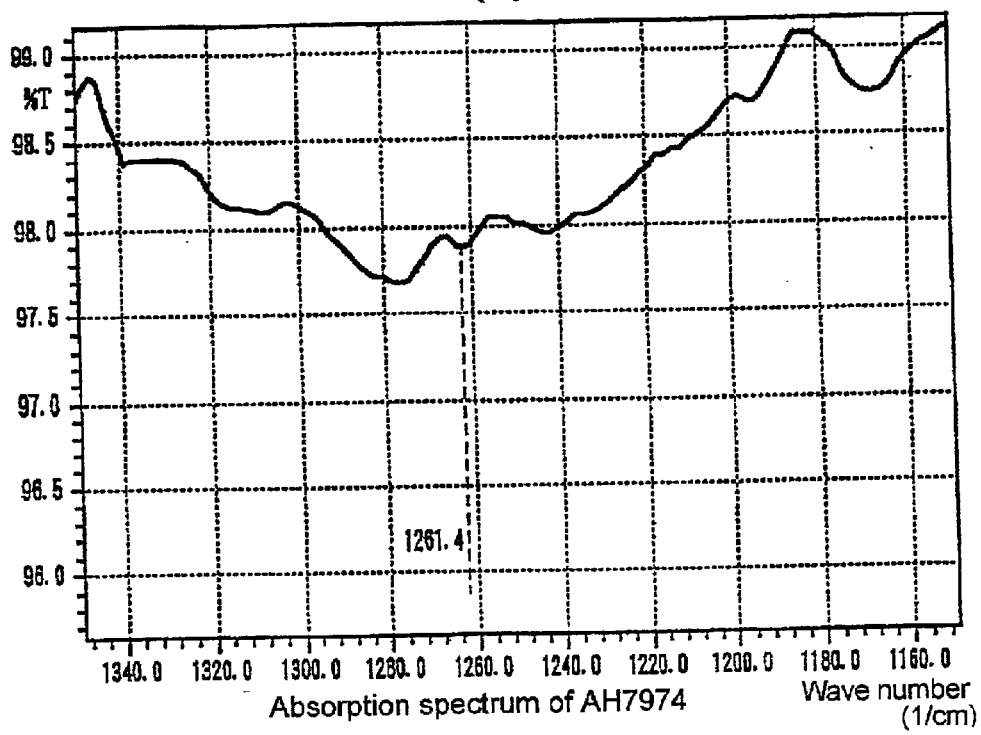
(A) Absorption spectrum of AH7974
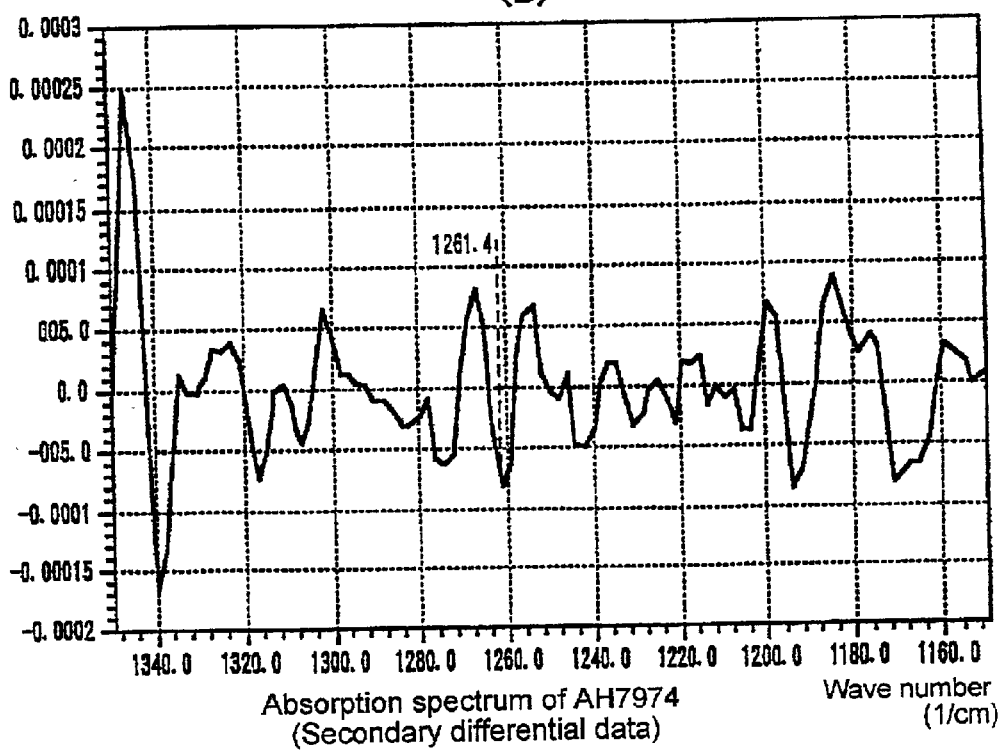
(B) Absorption spectrum of AH7974 (Secondary differential data)

Fig. 4
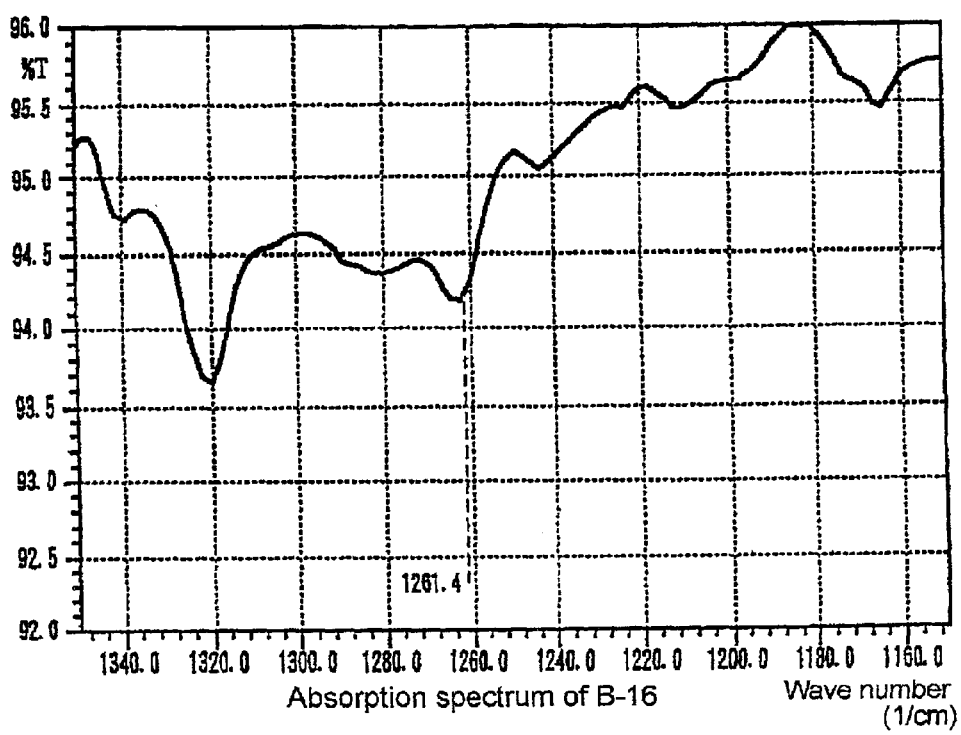
(A) Absorption spectrum of B-16
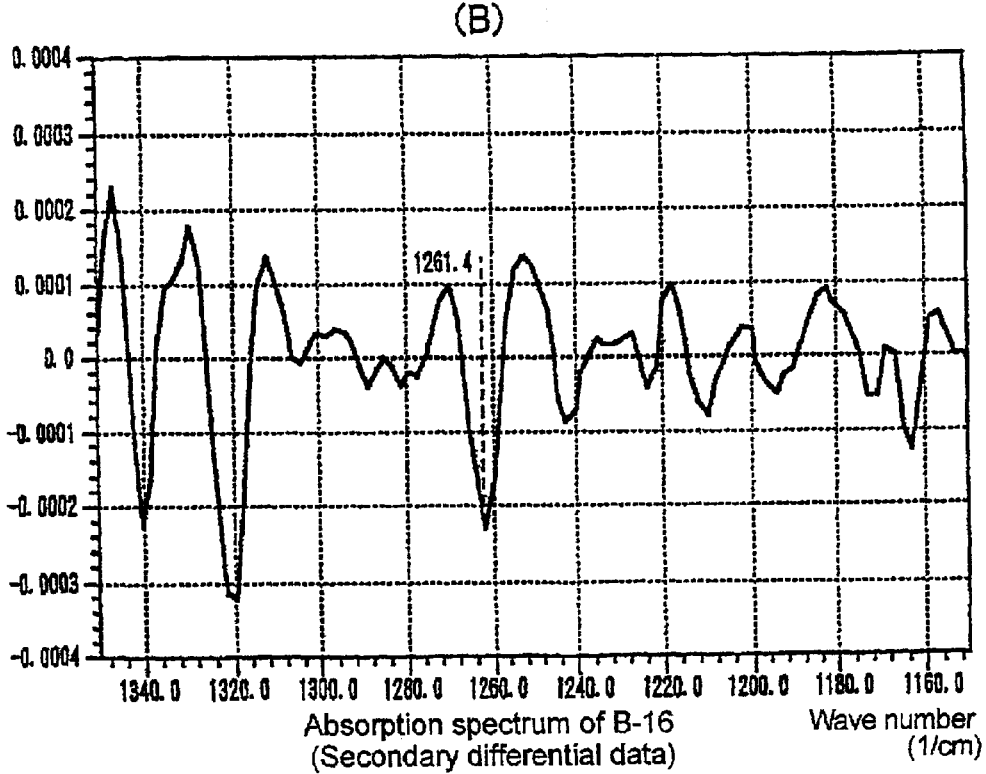
(B) Absorption spectrum of B-16 (Secondary differential data)

Fig. 5
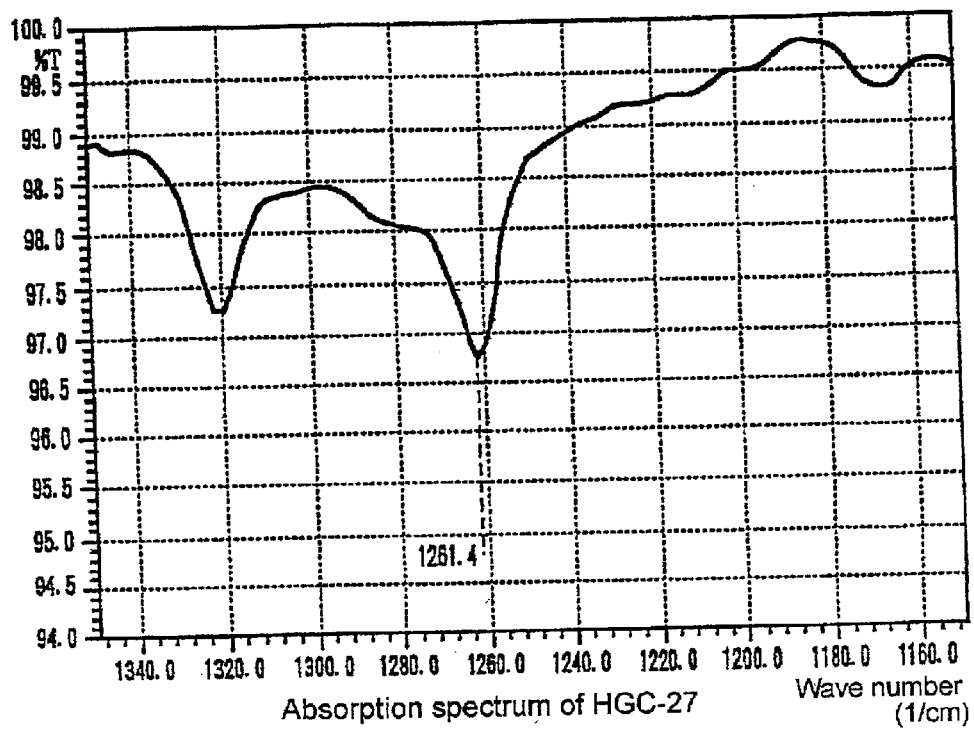
Absorption spectrum of HGC-27
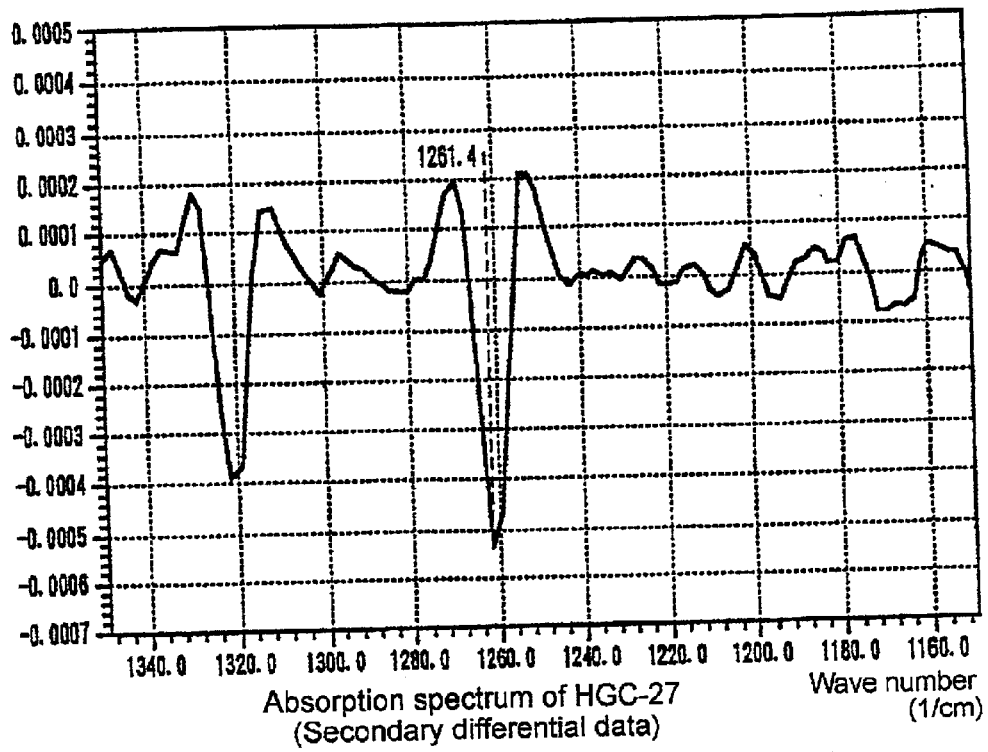
Absorption spectrum of HGC-27
(Secondary differential data)

Fig. 6
(A)
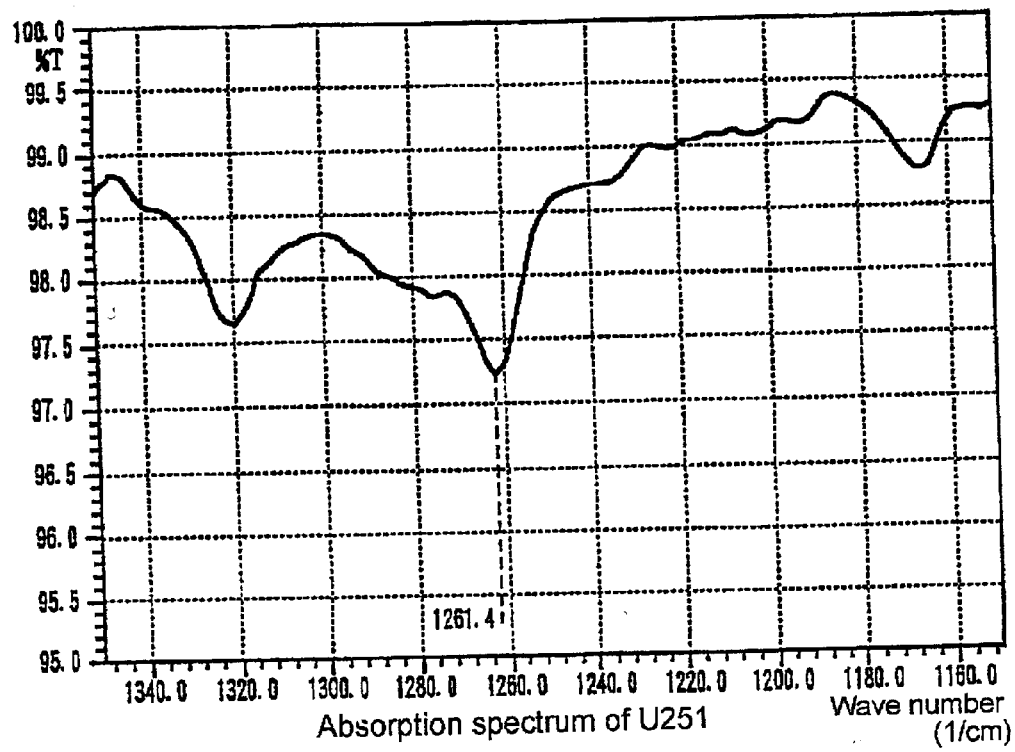
Absorption spectrum of U251
(B)
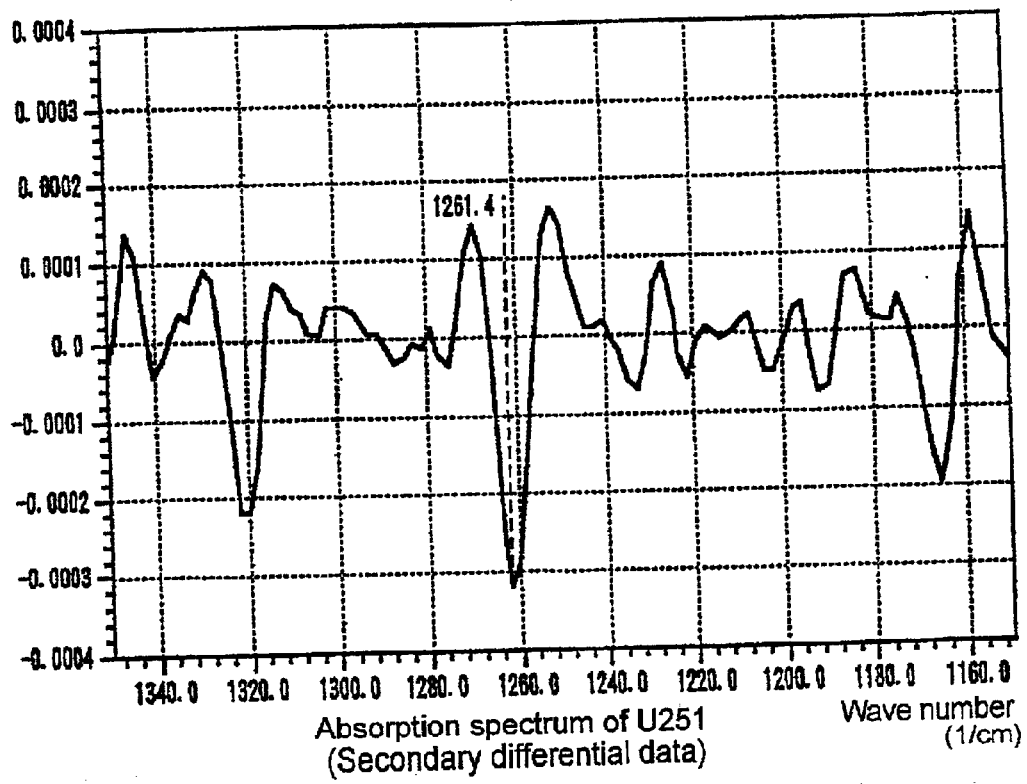
Absorption spectrum of U251
(Secondary differential data)

Fig. 7
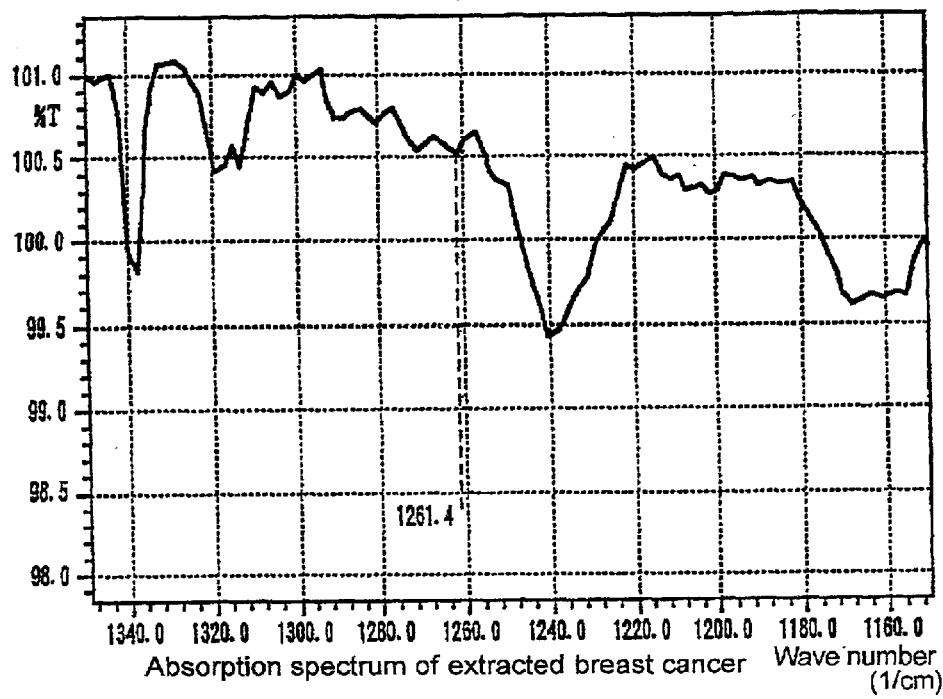
(A) Absorption spectrum of extracted breast cancer
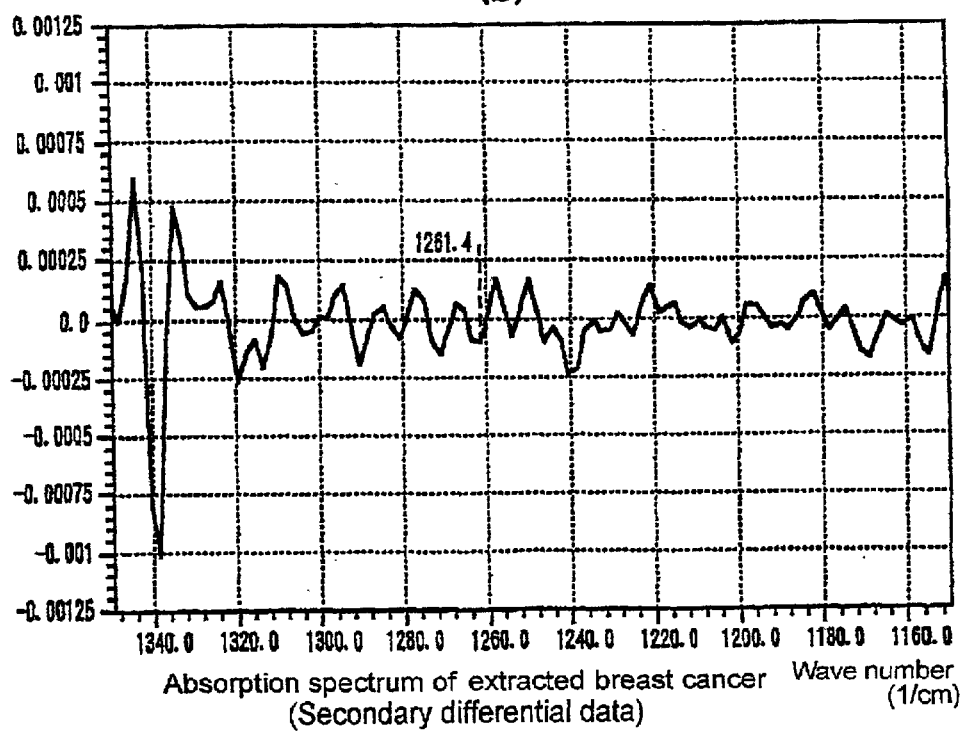
(B) Absorption spectrum of extracted breast cancer (Secondary differential data)

Fig. 11
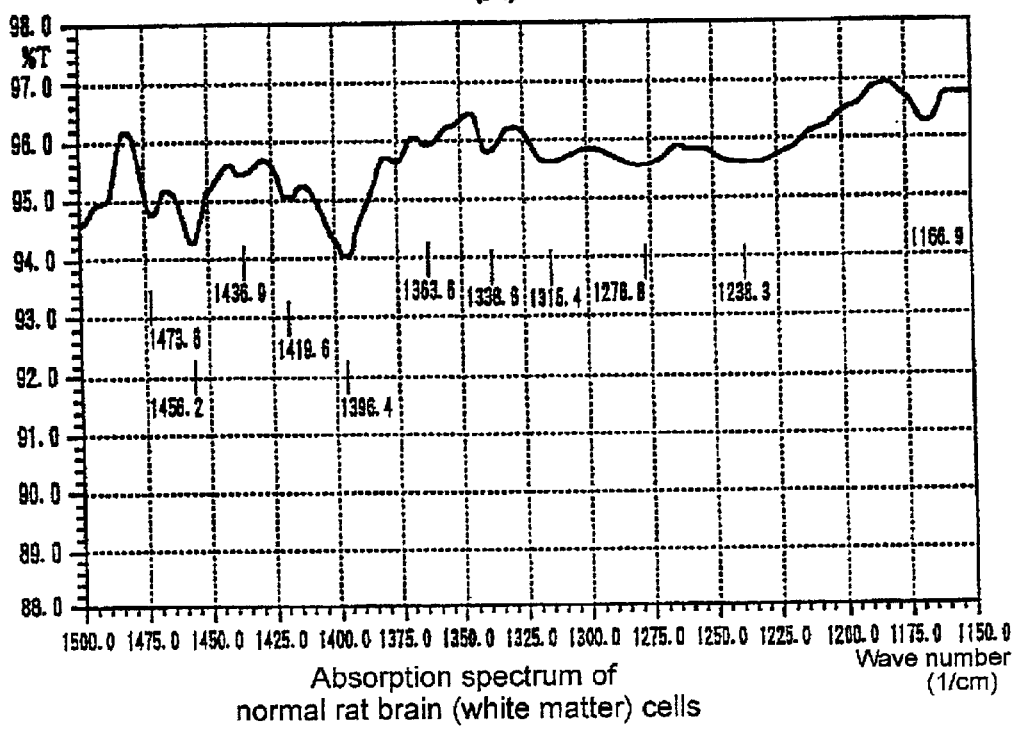
Absorption spectrum of
normal rat brain (white matter) cells
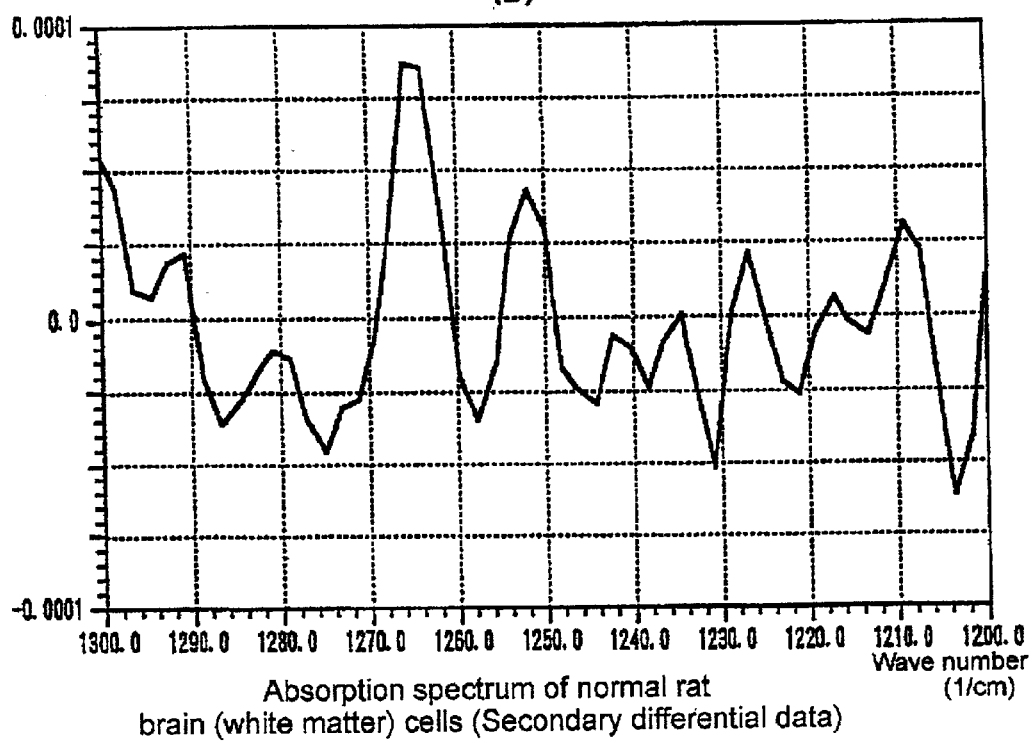
Absorption spectrum of normal rat
brain (white matter) cells (Secondary differential data)

Fig. 12
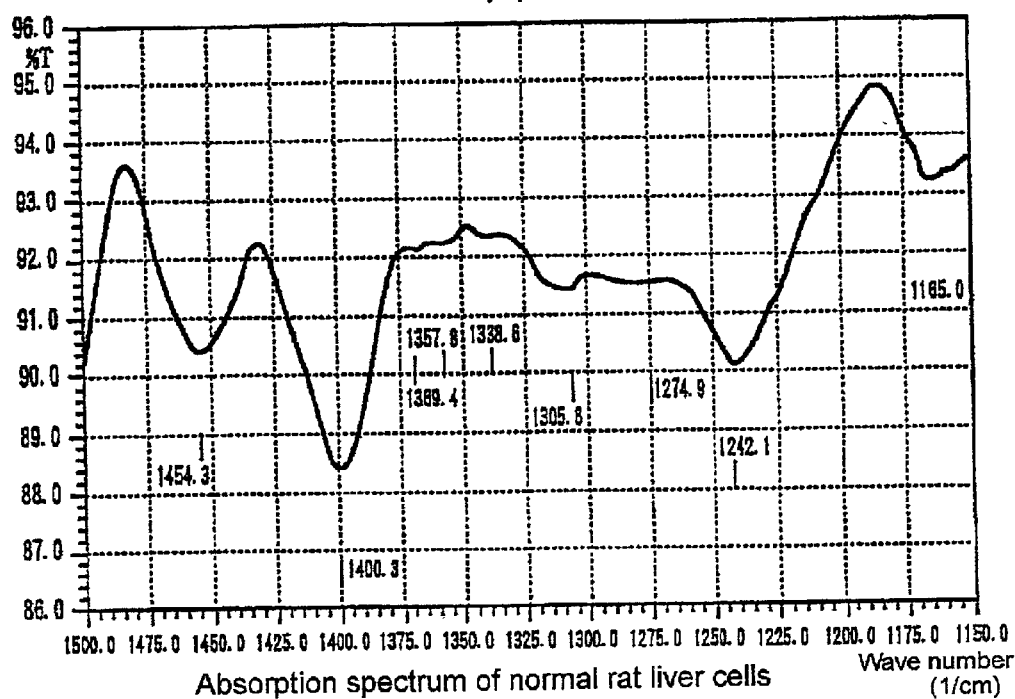
(A) Absorption spectrum of normal rat liver cells
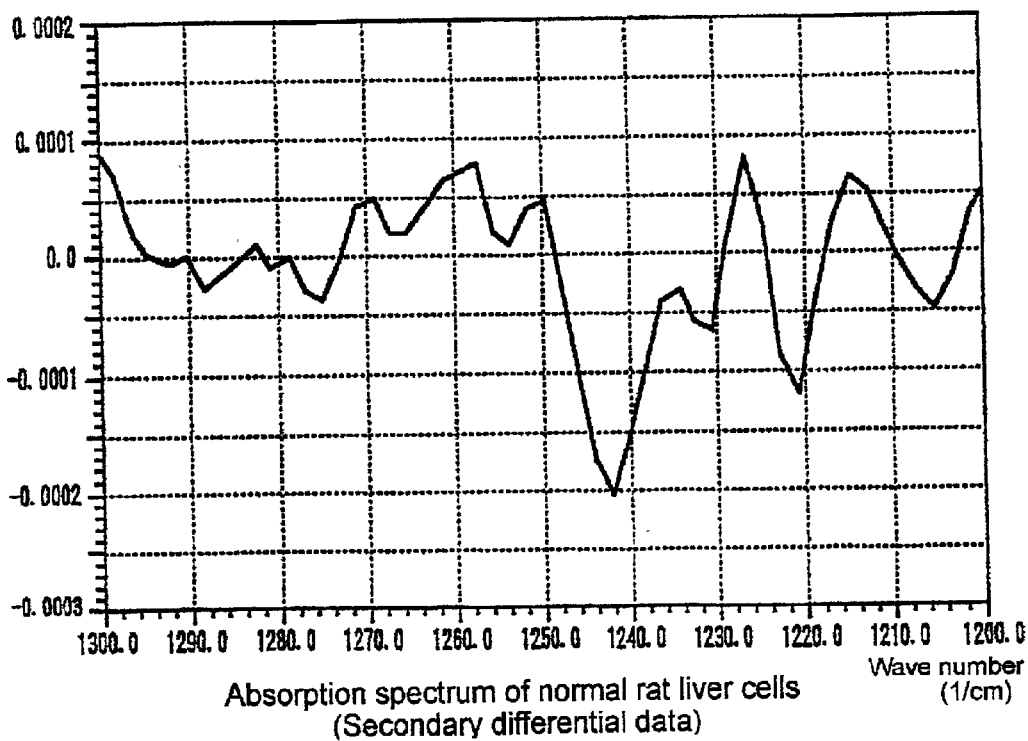
(B) Absorption spectrum of normal rat liver cells (Secondary differential data)

Fig. 13
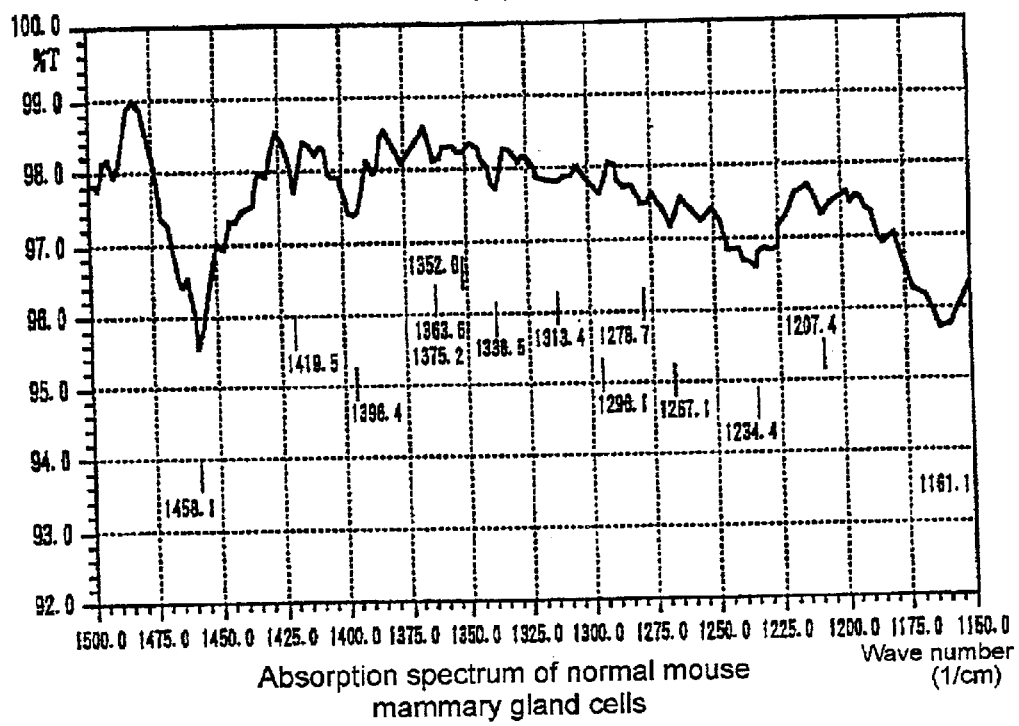
(A) Absorption spectrum of normal mouse mammary gland cells
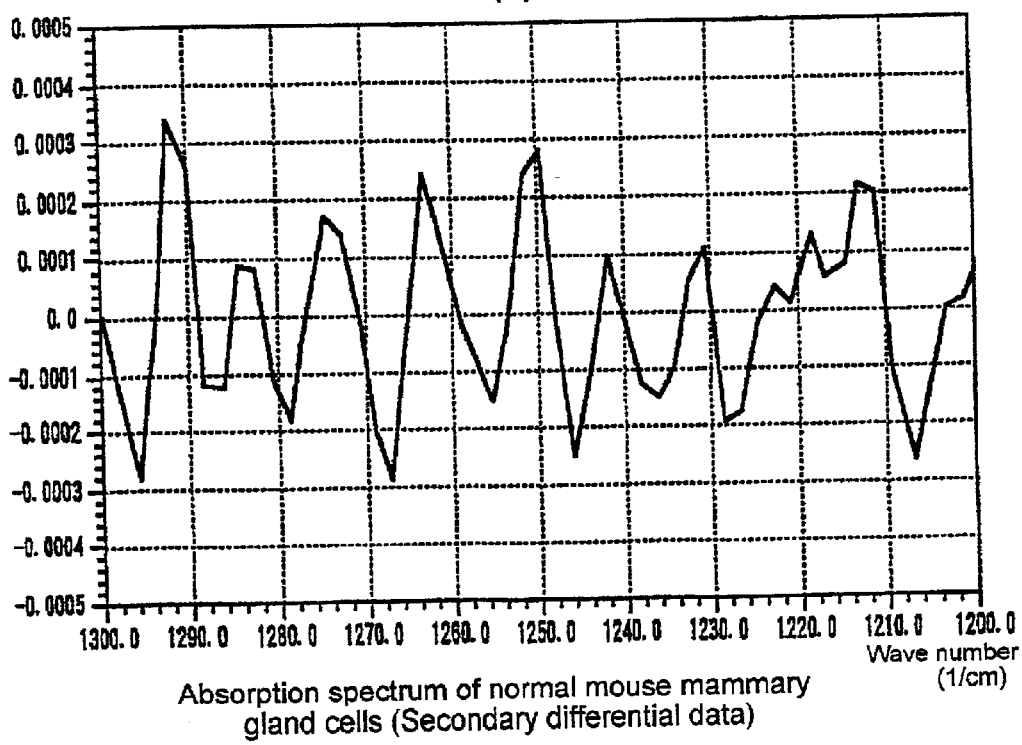
(B) Absorption spectrum of normal mouse mammary gland cells (Secondary differential data)

Fig. 14
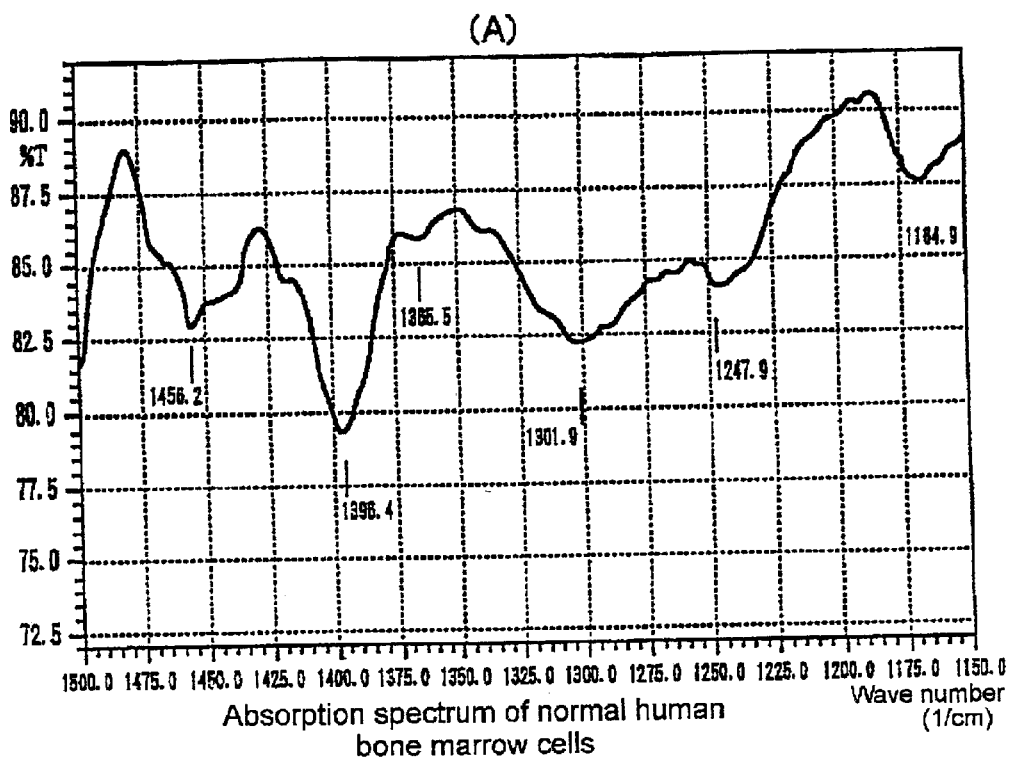
(A) Absorption spectrum of normal human bone marrow cells
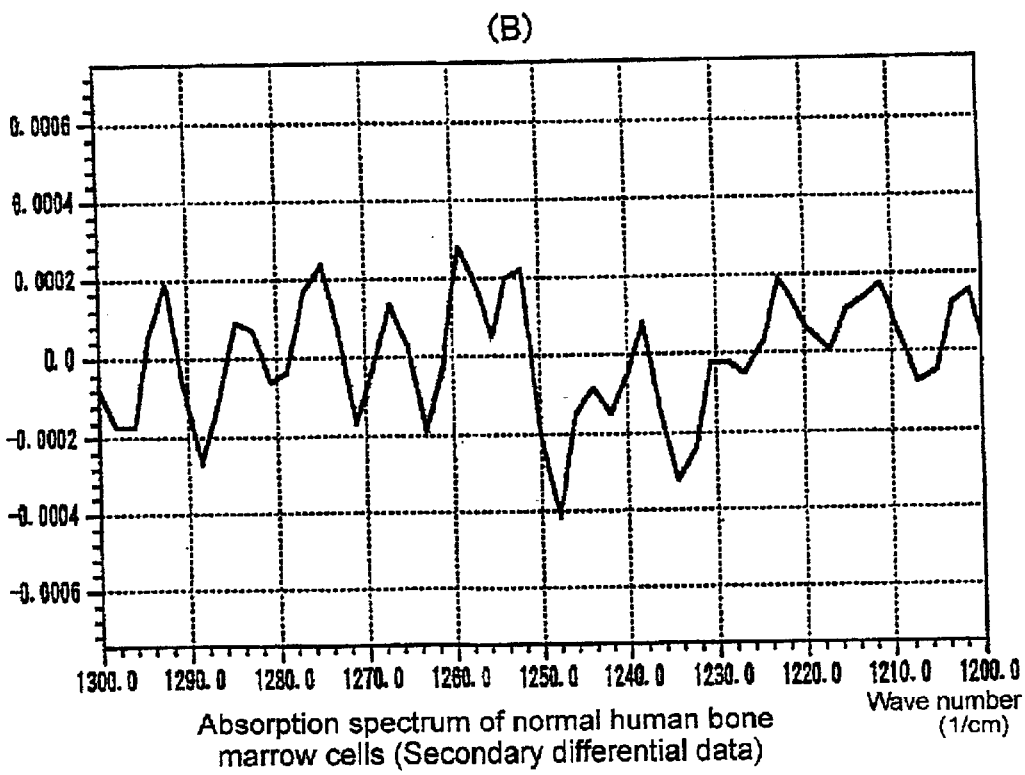
(B) Absorption spectrum of normal human bone marrow cells (Secondary differential data)

Fig. 16
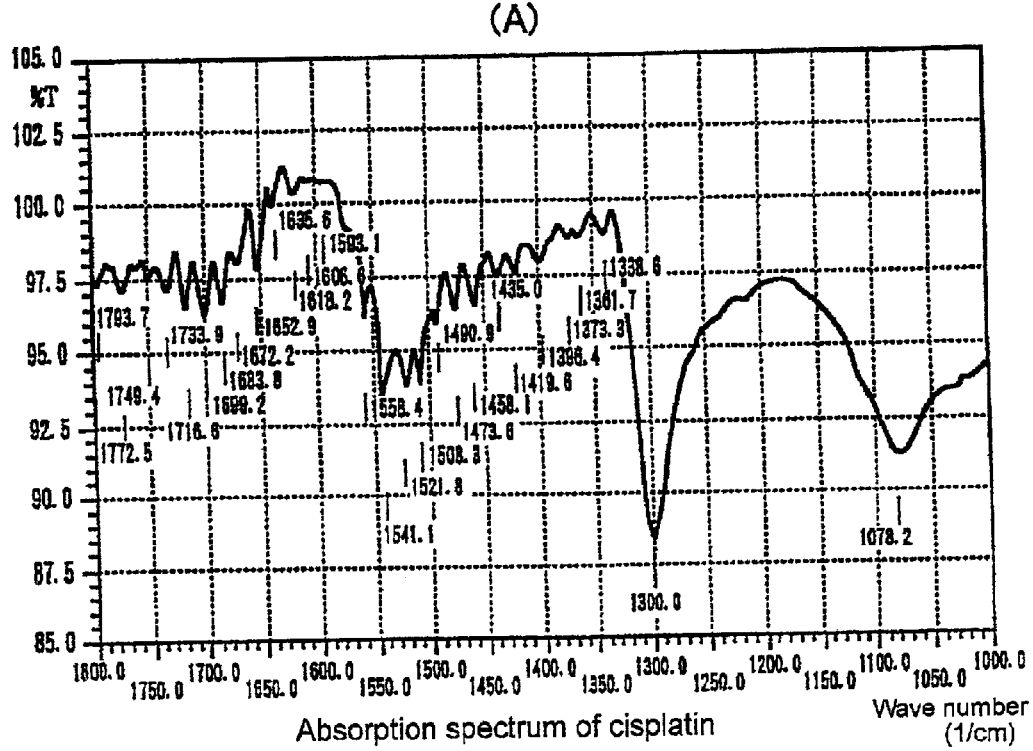
(A) Absorption spectrum of cisplatin
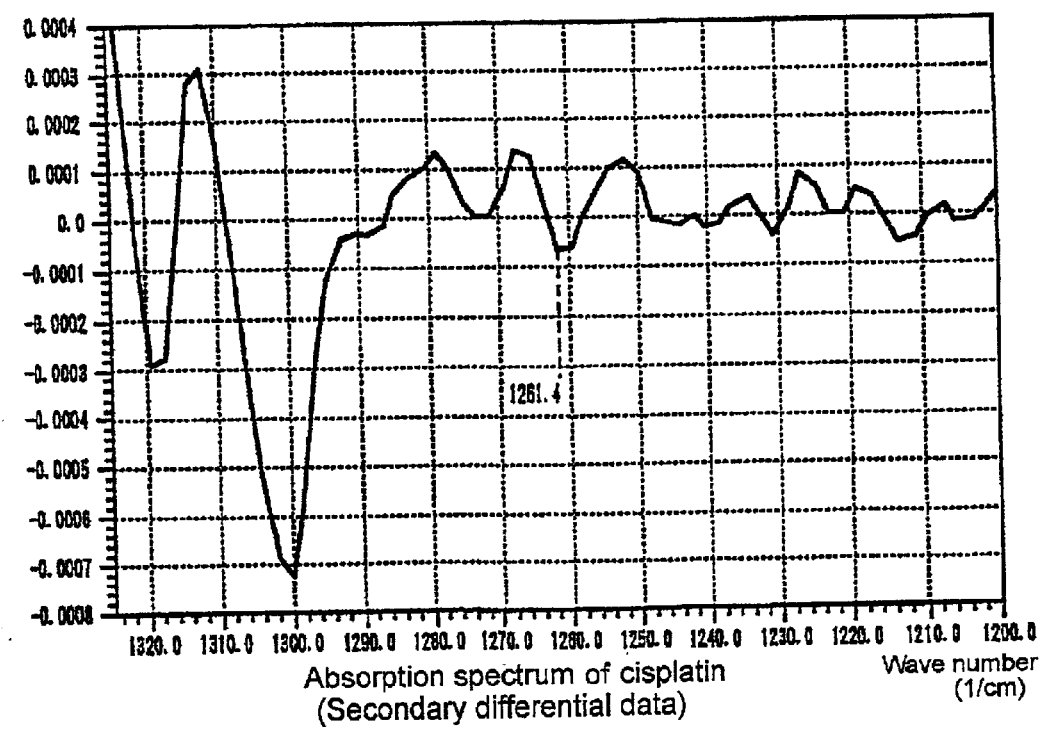
(B) Absorption spectrum of cisplatin (Secondary differential data)

Fig. 17
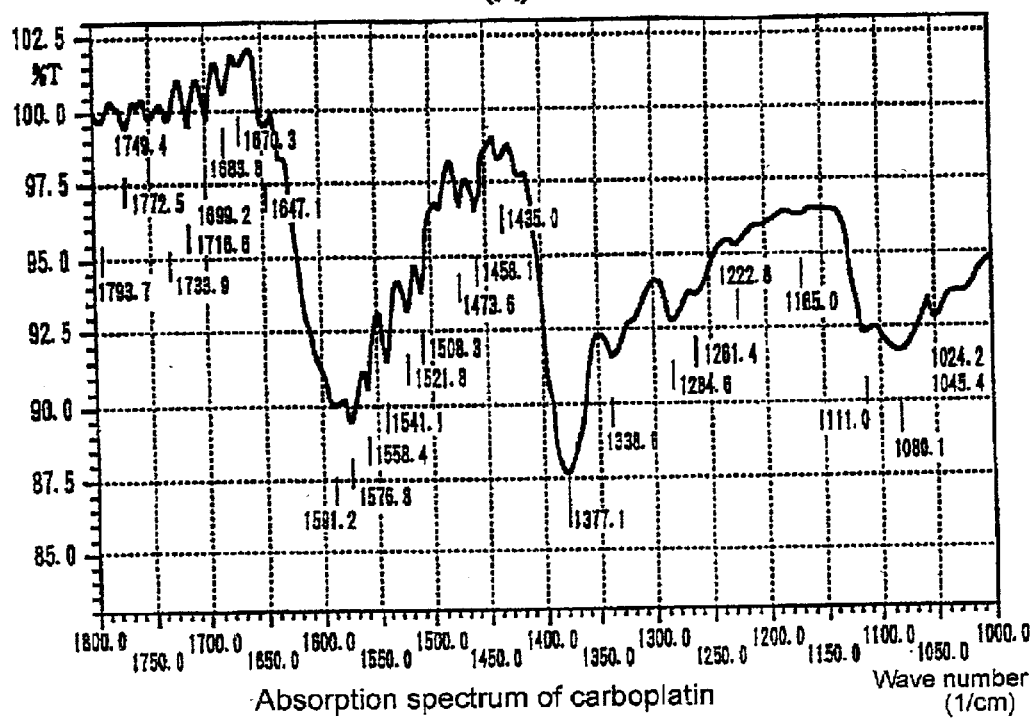
(A) Absorption spectrum of carboplatin
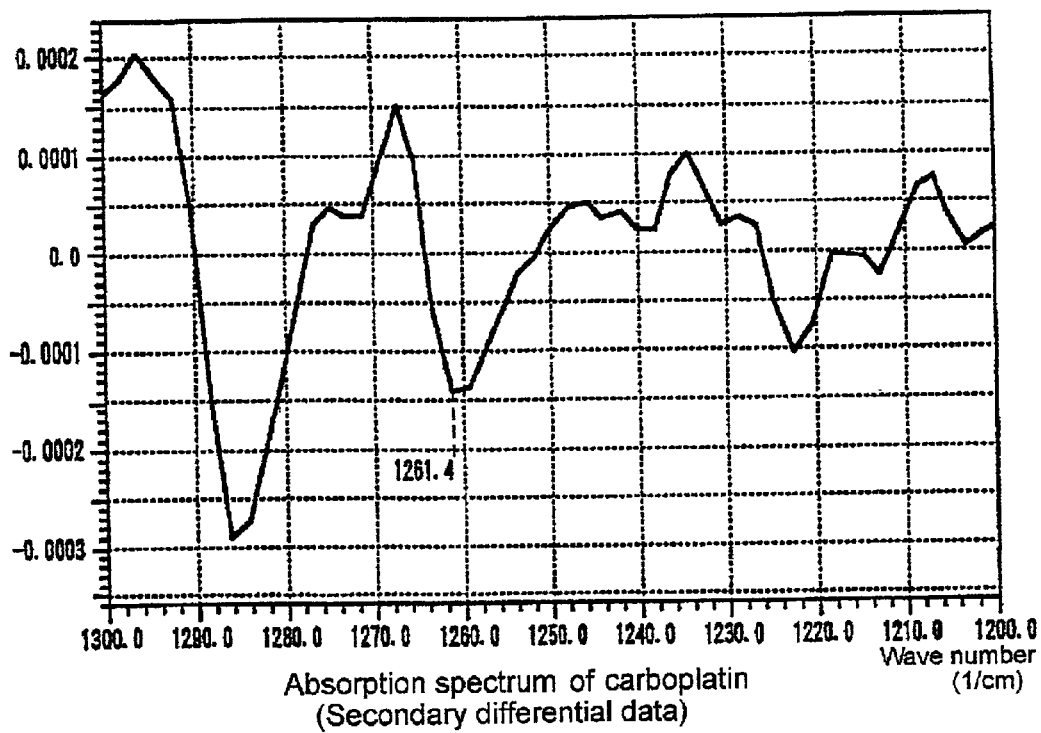
(B) Absorption spectrum of carboplatin (Secondary differential data)

Fig. 18
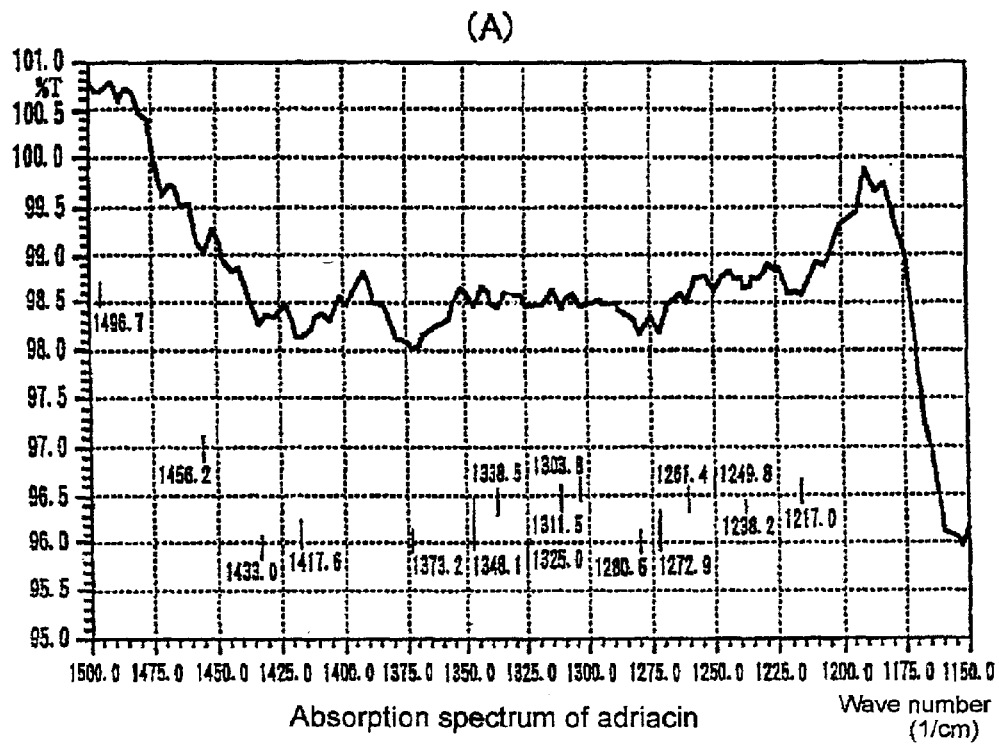
Absorption spectrum of adriacin
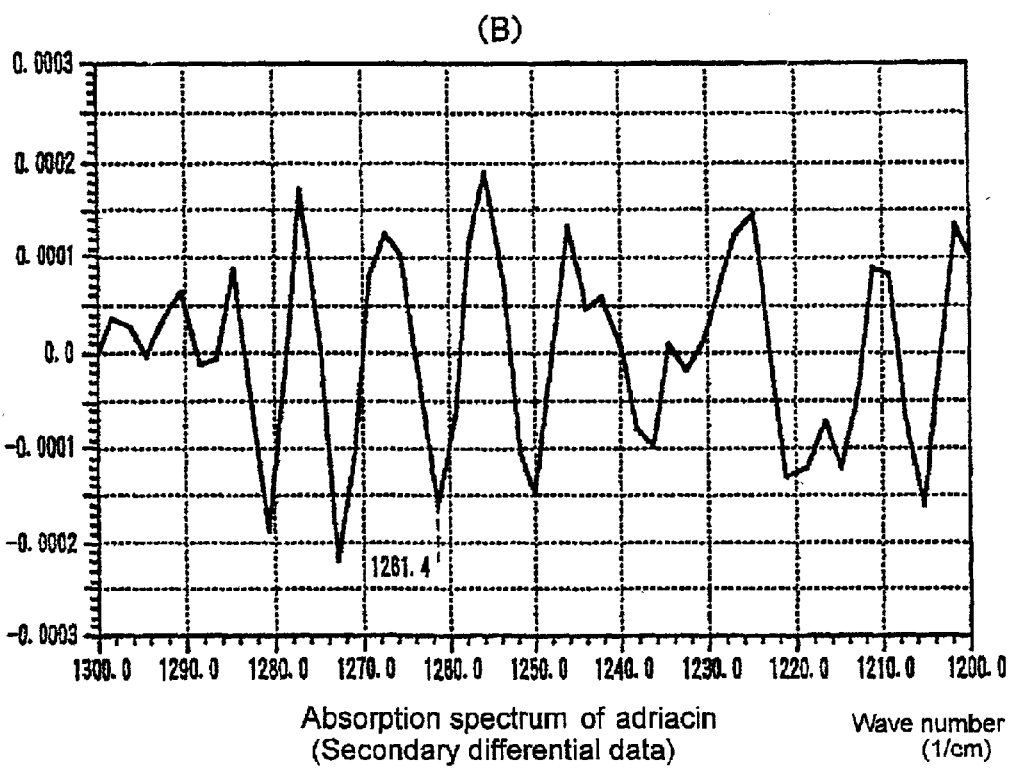
Absorption spectrum of adriacin
(Secondary differential data)

Fig. 19
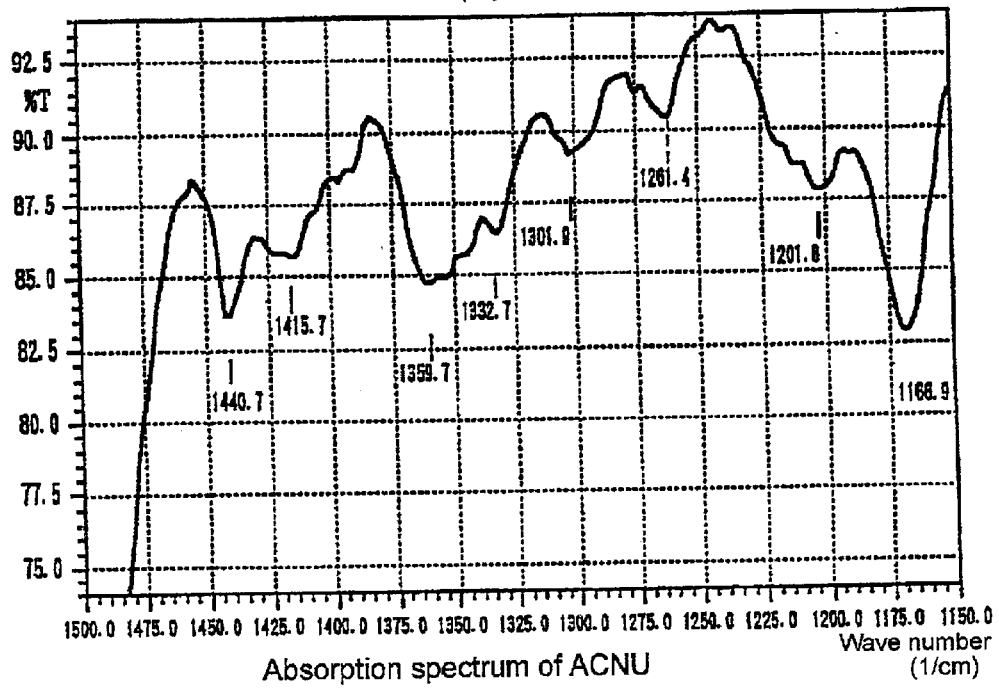
(A) Absorption spectrum of ACNU
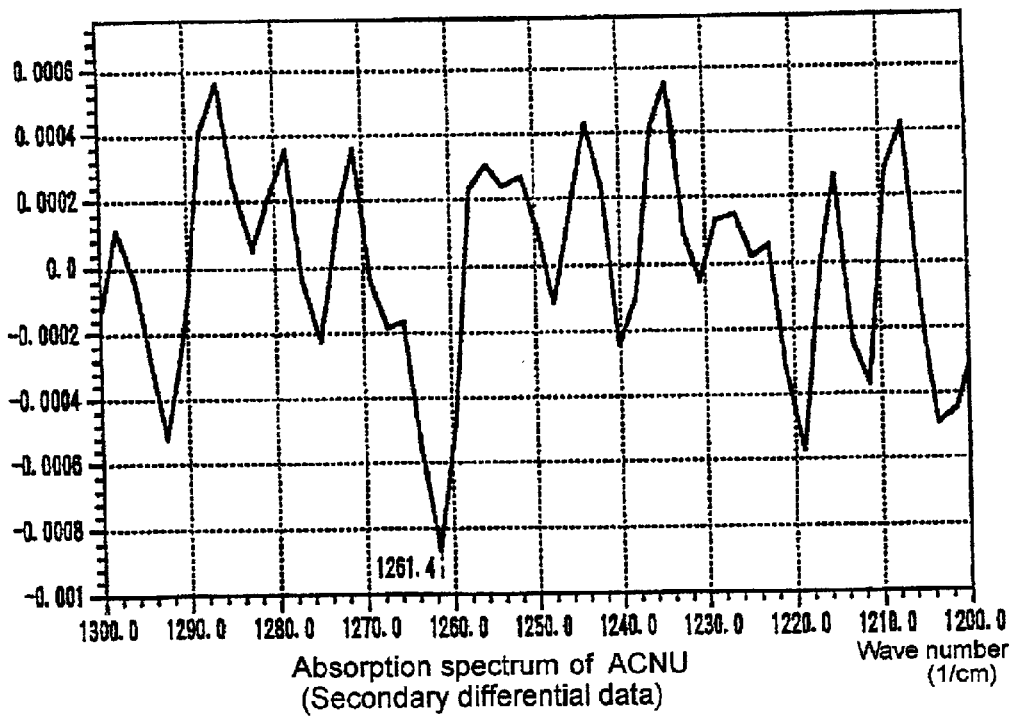
(B) Absorption spectrum of ACNU (Secondary differential data)

Fig. 25
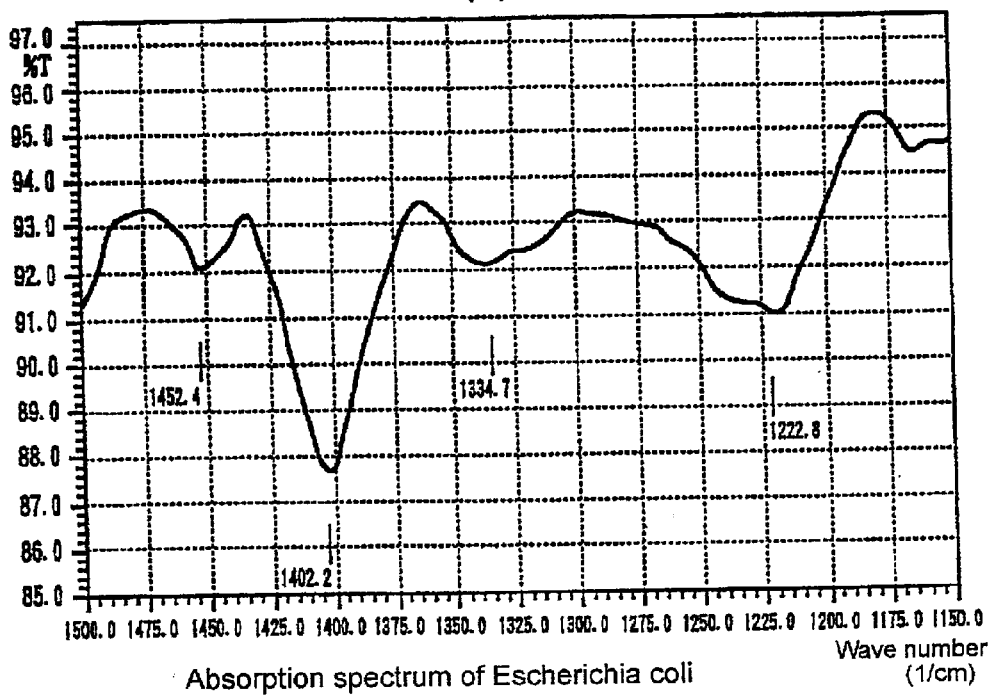
Absorption spectrum of Escherichia coli
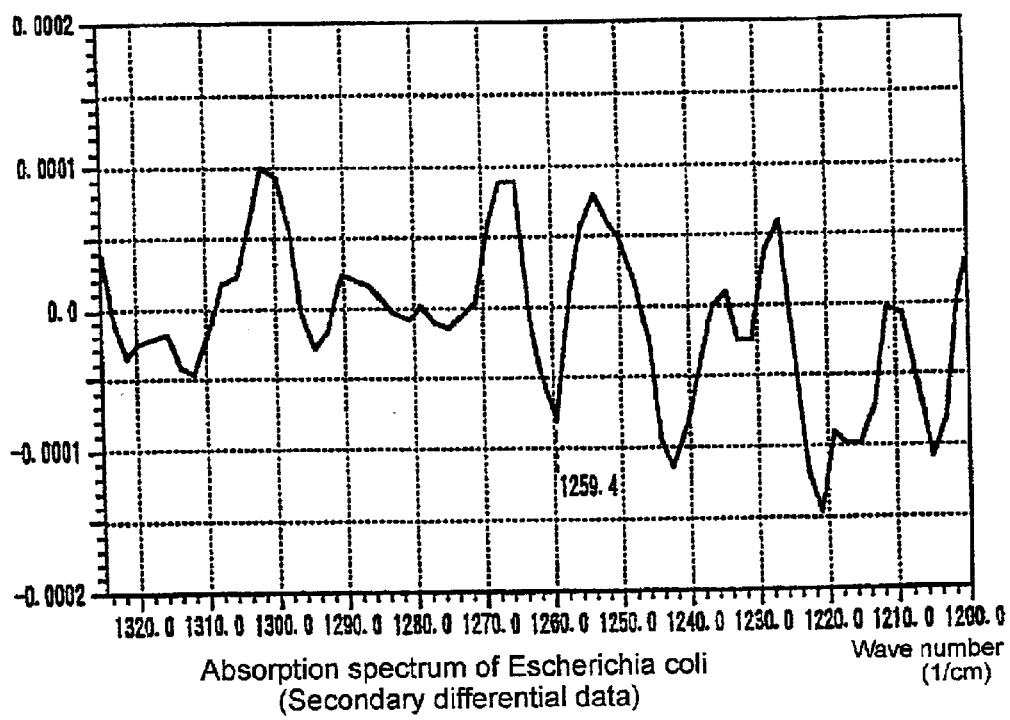
Absorption spectrum of Escherichia coli
(Secondary differential data)

Fig. 26
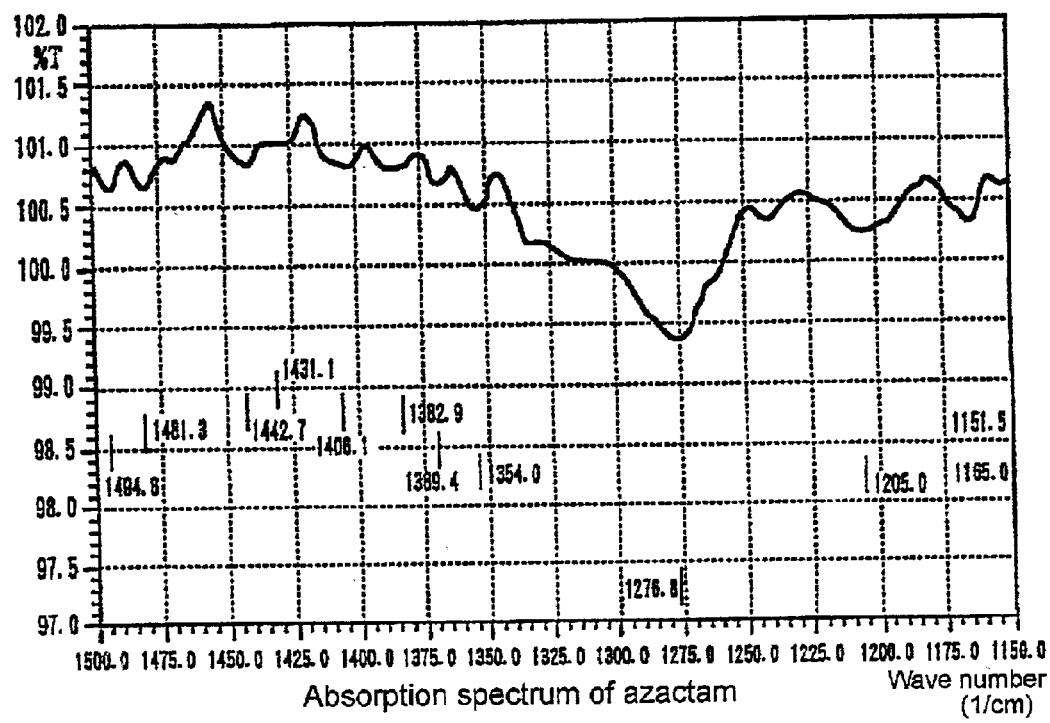
(A) Absorption spectrum of azactam
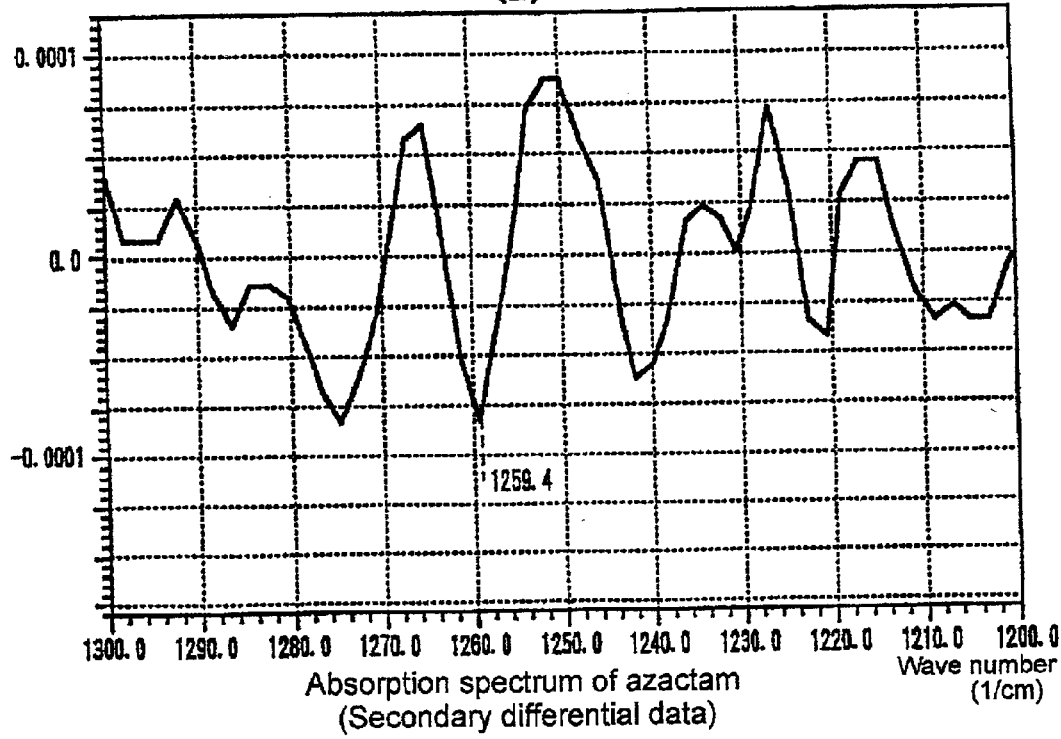
(B) Absorption spectrum of azactam (Secondary differential data)

Fig. 27
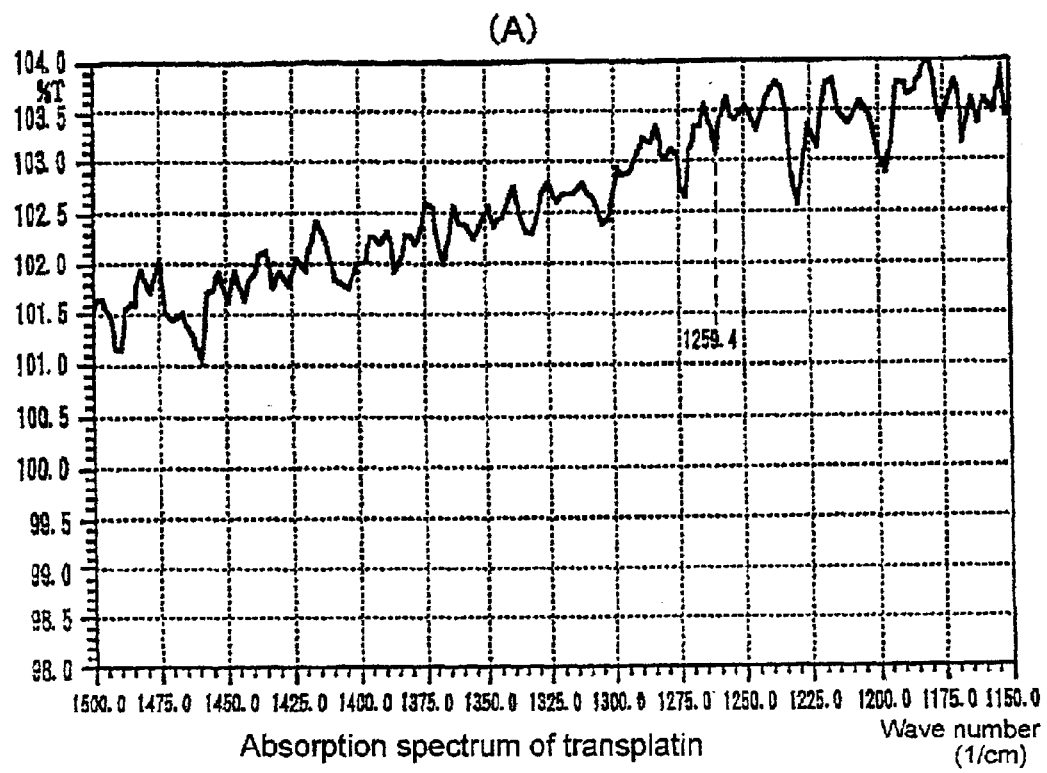
Absorption spectrum of transplatin
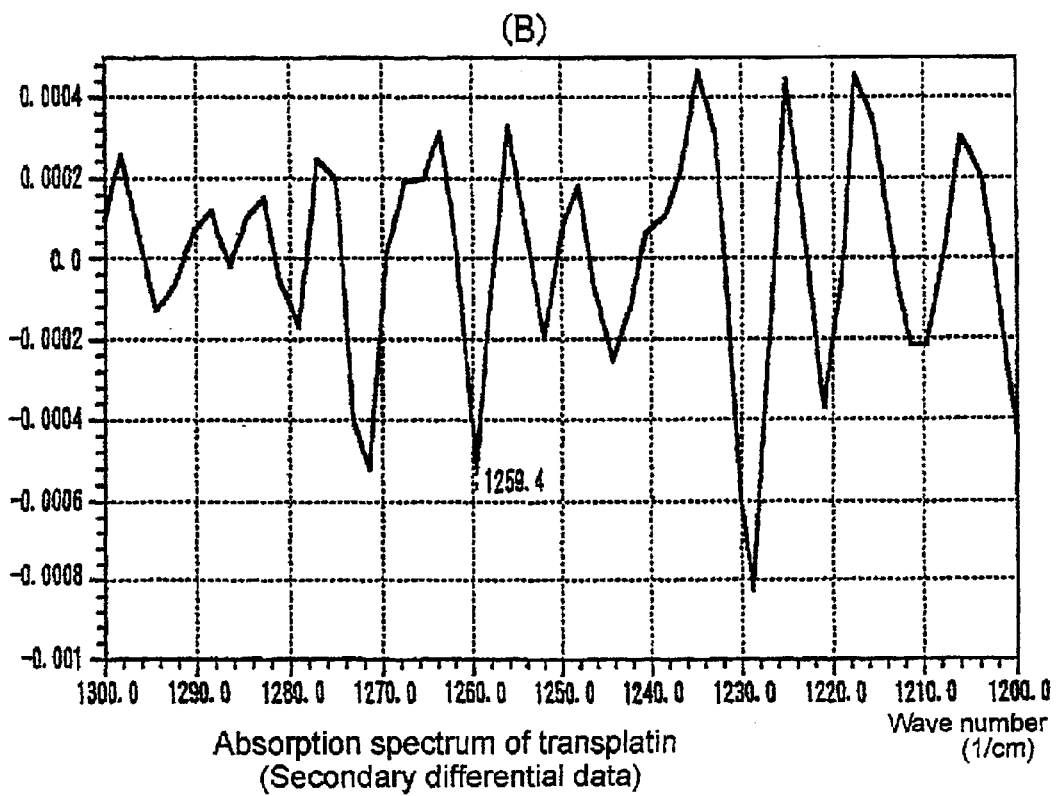
Absorption spectrum of transplatin
(Secondary differential data)

Disease type/condition determination method

Disease type/condition diagnostic apparatus 1

Drug screening method

Drug screening apparatus 2

DISEASE TYPE AND/OR CONDITION DETERMINATION METHOD AND APPARATUS AND DRUG SCREENING METHOD AND APPARATUS

This application is a continuation of PCT/JP00/01552 filed on Mar. 14, 2000.

TECHNICAL FIELD

The present invention relates to a disease type and/or condition determination method and apparatus, which enables a fast and reliable diagnosis to be made by identifying the specificity of cells and so forth based on physical aspects, and a drug screening method and apparatus, which enables efficient screening of a target drug.

BACKGROUND ART

There has been little research in the past that discusses, for example, the "definition of cancer cells" based on the "absolute specificity" of cancer cells relative to normal cells. Even with respect to carcinogenic genes and other cancer-related genes that have attracted particular attention in recent years, although there are currently reports stating that these are common to certain partial cell groups of cancer cells or are present in normal cells as well, these are merely a discussion relating to the "partial or relative specificity" of cancer cells. In other words, research thus far has consisted primarily of that which treats the cell membrane, enzymes and genes, etc. of cancer cells independently, attempts to indicate "absolute specificity" within them, and is biased towards a substance-oriented approach that includes identification of form and structural substances, elucidation of gene structure and so forth.

However, since there are vast numbers of atoms and molecules that compose cells, attempting to structurally define "what is meant by cancer cells" by sorting all of these vast numbers of substances and their forms, etc. into normal cells and cancer cells is considered to be nearly impossible. Consequently, in the case of research methods thus far that have employed a substance-oriented approach, it was difficult to identify what cancer cells mean and adequate results have yet to be obtained.

Therefore, as was previously disclosed in the prior applications of Japanese Unexamined Patent Publication No. Hei 9-285286, Japanese Unexamined Patent Publication No. Hei 9-285296, Japanese Unexamined Patent Publication No. Hei 9-286739 and Japanese Unexamined Patent Publication No. Hei 9-286740, the inventor of the present invention has proposed a method for clarifying the "absolute specificity" of bioactivity (organic substances such as cells, or organic bodies in the form of aggregates of those organic substances) based on physical aspects.

This method employs thermodynamic and statistical mechanical methods that perceives each cell in the form of a macroscopic system, and indicates the "absolute specificity" of its bioactivity by focusing on the energy state of that system. Namely, this method entraps the biochemical mechanism of bioactivity within a black box, identifies the atoms and molecules that serve as the constituent elements of cells and so forth by spectral analysis that includes their quantum states, and then controls their bioactivity. More specifically, this involves, for example, detecting the characteristic spectrum of cancer cells and then planning and designing an anti-cancer agent having a spectrum that interacts with the resonance of that characteristic spectrum.

However, in the determination of the type of a disease and its condition, a method is desired that allows rapid evaluation of condition and so forth based on viable cells sampled from a specimen. In addition, in the development of a drug and so forth, a screening method is required that is able to efficiently screen for an organism or substance having the target effect or ability among a large population.

The methods of the inventions of the prior applications previously mentioned made it possible to rapidly perform determination of the type and condition of a disease or selection of a drug by an extremely simple method in the form of spectral analysis. However, the accuracy of that determination was not always adequate, and there is still a strong desire for the realization of a more efficient screening method.

In consideration of the above points, the object of the present invention is to provide a disease type and/or condition determination method and apparatus that enable rapid and accurate evaluation, along with a drug screening method and apparatus that enables more efficient screening of a target drug, by performing spectral analysis of the energy state of cells and drugs and processing those results using a plurality of spectra as indices.

DISCLOSURE OF THE INVENTION

In order to achieve the above object, the disease type and/or condition determination method according to the present invention determines the type and/or condition of a disease by analyzing the absorption or emission spectrum in a specific region of cells obtained from a specimen, and using the appearance of spectra corresponding to at least two wave numbers within the above specific region as indices in accordance with the results of the spectral analysis.

In such a method, in addition to being able to determine the type and/or condition of a disease by a simple method in the form of performing spectral analysis of cells obtained from a specimen, by evaluating and processing the results of spectral analysis by using the appearance of spectra corresponding to at least two wave numbers in a specific wavelength region as indices, determination of disease type and so forth can be performed more reliably.

With respect to the above method for determining disease type and/or condition, the above specific region should include the infrared region (and preferably any part or the entire range of 10.0 to 13157.9 $cm^{-1}$). In addition, this method is able to determine whether or not the specimen is cancer, and in this case, one of the wave numbers of the spectrum used as an index should be 1261 $cm^{-1}$ (and preferably 1261.4 $cm^{-1}$). Moreover, it is also possible to determine whether or not a cell has specific bacteria, and drug resistance bacteria are a specific example of the above specific bacteria. In addition, it is also possible to determine whether or not a cell is infected by a specific virus.

In addition, the apparatus for diagnosing disease type and/or condition according to the present invention is composed of spectral analysis means that analyzes the absorption spectrum or emission spectrum in a specific region of cells obtained from a specimen, and diagnostic means that diagnoses disease type and/or condition by using the appearance of spectra corresponding to at least two wave numbers within the above specific region as indices in accordance with the results of spectral analysis obtained with the spectral analysis means.

The drug screening method according to the present invention performs screening of a target drug by analyzing the absorption spectrum or emission spectrum of the target drug in a specific region using the appearance of spectra corresponding to at least two wave numbers within the specific region as indices in accordance with the results of the spectral analysis.

According to the drug screening method, in addition to enabling rapid screening by using a simple method in the form of spectral analysis of a target drug, by performing screening by using the appearance of spectra corresponding to at least two wave numbers within a specific region as indices, a drug having the desired effect and capability can be more reliably extracted.

In the above drug screening method, the above specific region should include the infrared region (and preferably any part or the entire range of 10.0 to 13157.9 $cm^{-1}$). In addition, screening can be performed using an anti-cancer agent for the target drug, and in this case, one of the wave numbers of the spectrum used as an index should be 1261 $cm^{-1}$ or 1163 $cm^{-1}$ (and preferably 1261.4 $cm^{-1}$ or 1163.1 $cm^{-1}$). Moreover, it is also possible for the target drug to be an antibiotic, and a specific example of an antibiotic is that which is effective against drug resistance bacteria. In addition, the target drug can also be an anti-viral agent.

The drug screening apparatus according to the present invention is composed of spectral analysis means that analyzes the absorption or emission spectrum in a specific region of a target drug, and screening means that screens the above target drug by using the appearance of spectra corresponding to at least two wave numbers in the above specific region as indices in accordance with the results of spectral analysis obtained with the said spectral analysis means.

BRIEF DESCRIPTION OF THE DRAWINGS

FIGS. 2A and 2B show graphs illustrating the results of performing spectral analysis using cultured cells derived from ascitic liver cancer as a sample.

FIGS. 4A and 4B show graphs illustrating the results of performing spectral analysis using cultured cells derived from mouse malignant melanoma as a sample.

FIGS. 5A and 5B show graphs illustrating the results of performing spectral analysis using cultured cells derived from human stomach cancer as a sample.

FIGS. 6A and 6B show graphs illustrating the results of performing spectral analysis using cultured cells derived from human glioblastoma as a sample.

FIGS. 7A and 7B show graphs illustrating the results of performing spectral analysis using cancer cells extracted from a breast cancer patient as a sample.

FIGS. 11A and 11B show graphs illustrating the results of performing spectral analysis using normal rat brain (white matter) cells as a sample.

FIGS. 12A and 12B show graphs illustrating the results of performing spectral analysis using normal rat liver cells as a sample.

FIGS. 13A and 13B show graphs illustrating the results of performing spectral analysis using normal mouse mammary gland cells as a sample.

FIGS. 14A and 14B show graphs illustrating the results of performing spectral analysis using normal human bone marrow cells as a sample.

FIGS. 16A and 16B show graphs illustrating the results of performing spectral analysis using cisplatin as a sample.

FIGS. 17A and 17B show graphs illustrating the results of performing spectral analysis using carboplatin as a sample.

FIGS. 18A and 18B show graphs illustrating the results of performing spectral analysis using doxorubicin hydrochloride (Adriacin) as a sample.

FIGS. 19A and 19B show graphs illustrating the results of performing spectral analysis using nimustine hydrochloride (ACNU) as a sample.

FIGS. 25A and 25B show graphs illustrating the results of spectral analysis in the case of using *Escherichia coli* as a sample.

FIGS. 26A and 26B show graphs illustrating the results of spectral analysis in the case of using aztreonam (Azactam) as a sample.

FIGS. 27A and 27B show graphs illustrating the results of spectral analysis in the case of using transplatin as a sample.

BEST MODE FOR CARRYING OUT THE INVENTION

To begin with, an explanation is provided of the basic matters of the present invention.

As was previously described, the present invention adopts the standpoint of employing thermodynamic and statistical mechanical methods in perceiving a single cell in the form of a macroscopic system and elucidating the absolute specificity of cells and so forth by focusing on the energy state of that system. Thus, in the present invention, cells are considered to be "a thermodynamically unbalanced open system", and for example, cancer cells and normal cells, etc. can be observed in the form of differences in the states of that system (quantum intrinsic energy state).

Figure 1:
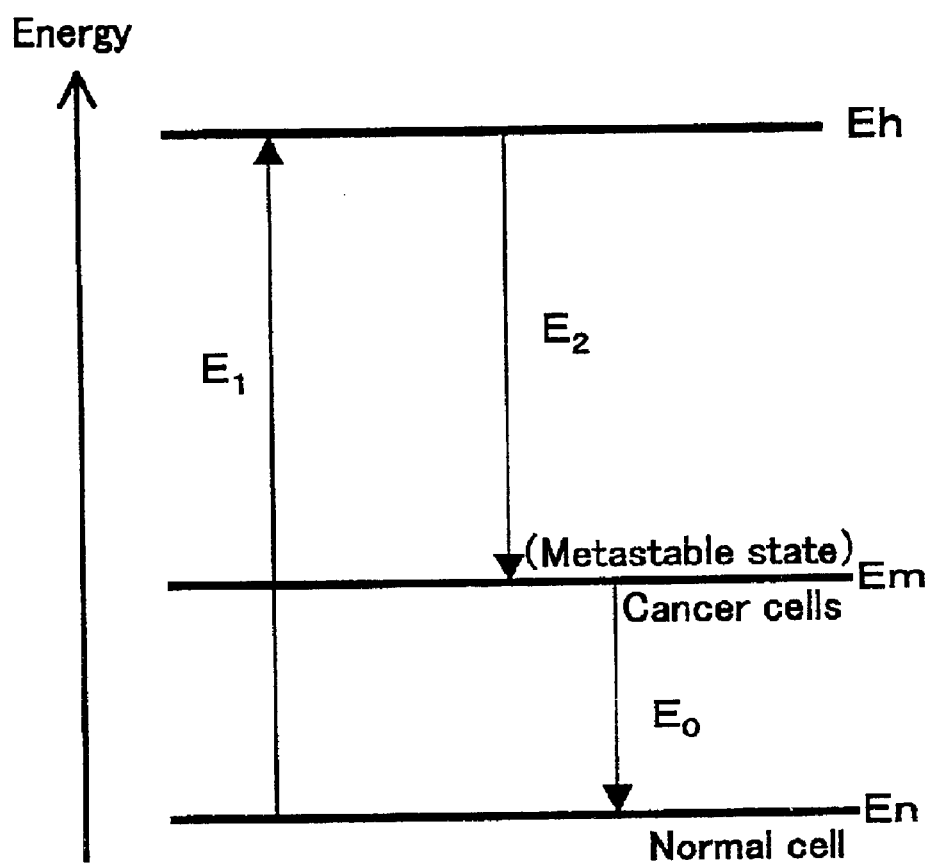
FIG. 1 is a diagram showing a three-state maser model for explaining the fundamental items of the present invention.

Differences in the states of the above cancer cell and normal cell systems can be easily explained by using a model of three-state maser as shown, for example, in FIG. 1. Here, the three energy states are represented by Eh, Em and En (the size relationship of the energy levels is Eh>Em>En. It should be noted that the reason for using a three-state maser model is to avoid making the explanation excessively complex, while in actuality, it would be more appropriate to use a model of a system depicting numerous energy states.

In the case of FIG. 1, normal cell are in state En, while those cells that successfully change to state Em (metastable state) after passing through state Eh as a result of those normal cells absorbing suitable energy $E_1$ are considered to be cancer cells. In addition, contact with a different system having an energy level that is able to resonate with this system is necessary to inductively cause the cancer cells to change from metastable state Em to state En or its vicinity. Anti-cancer agents share this energy level and this is thought to be the reason for their selective action against cancer cells.

The following provides a detailed explanation of the validity of the above approach while indicating experimental results. It should be noted that in the following explanation, while the explanation focuses primarily on the use of analysis of the energy absorption spectrum, the present invention can also be carried out by using analysis of the energy emission spectrum.

In order for the above approach to acquire validity, it is first necessary to confirm the fact that there exists an energy level that is unique and common to a plurality of cancer cells. Therefore, measurement of the infrared absorption spectrum was performed using FT-IR (Fourier-Transform Infrared spectroscopy) and cultured viable cancer cells sampled from a specimen for the sample. The FT-IR system is a typical measuring system for analyzing absorption peaks by determining the spectrum by irradiating light onto the sample and performing Fourier transformation on the two-beam interference curve of infrared light that is transmitted or reflected. For actual measurement, FT-IR systems were used in which the wave number measurement error is within ±0.1 cm$^{-1}$ (Shimadzu: FTIR8100 and 8300), and sample treatment and measurement were performed at room temperature. Furthermore, caution was taken during measurement by FT-IR so that the sample cells were dispersed in the measured region.

FIGS. 2 through 7 show examples of the results of performing spectral analysis of various types of cancer cells. In (A) of each figure, the infrared absorption spectrum measured by FT-IR is indicated on the horizontal axis as a wave number (cm$^{-1}$), while in (B) of each figure, the data of (A) is processed by differentiating to the second order so as to clarify the wave number of the absorption peaks.

Figure 3:
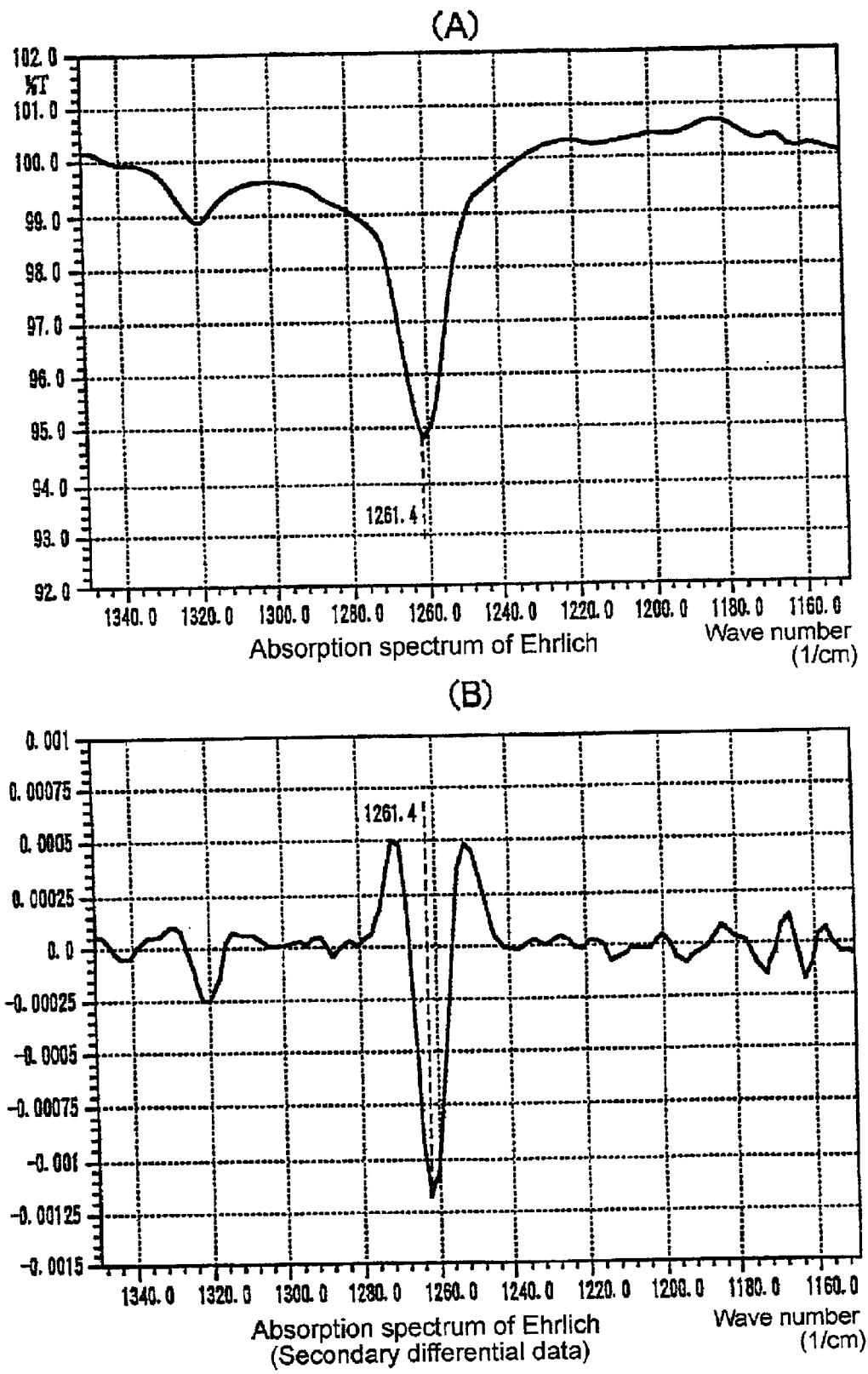
FIGS. 3A and 3B show graphs illustrating the results of performing spectral analysis using cultured cells derived from mice breast cancer as a sample.

More specifically, FIG. 2 illustrates data in the case of using as a sample cultured cells derived from rat ascitic liver cancer (AH7974), FIG. 3 that of cultured cells derived from mouse breast cancer (Ehrlich), FIG. 4 that of cultured cells derived from mouse malignant melanoma (B16), FIG. 5 that of cultured cells derived from human stomach cancer (HGC27), FIG. 6 that of cultured cells derived from human glioblastoma (U251), and FIG. 7 that of cancer cells extracted from a breast cancer patient.

It was found from FIGS. 2 through 7 that a wave number of 1261.4 cm$^{-1}$ exists as a wave number of the infrared absorption spectrum common to all cancer cells, and that there exists a group of the infrared absorption spectrum corresponding to at least two wave numbers in each cancer cell. The former is a fact that was also described in the previously mentioned prior publications, and the data indicated here serves to support this fact. In addition, the former is a fact that correlates with contents that characterize the present invention.

Figure 8:
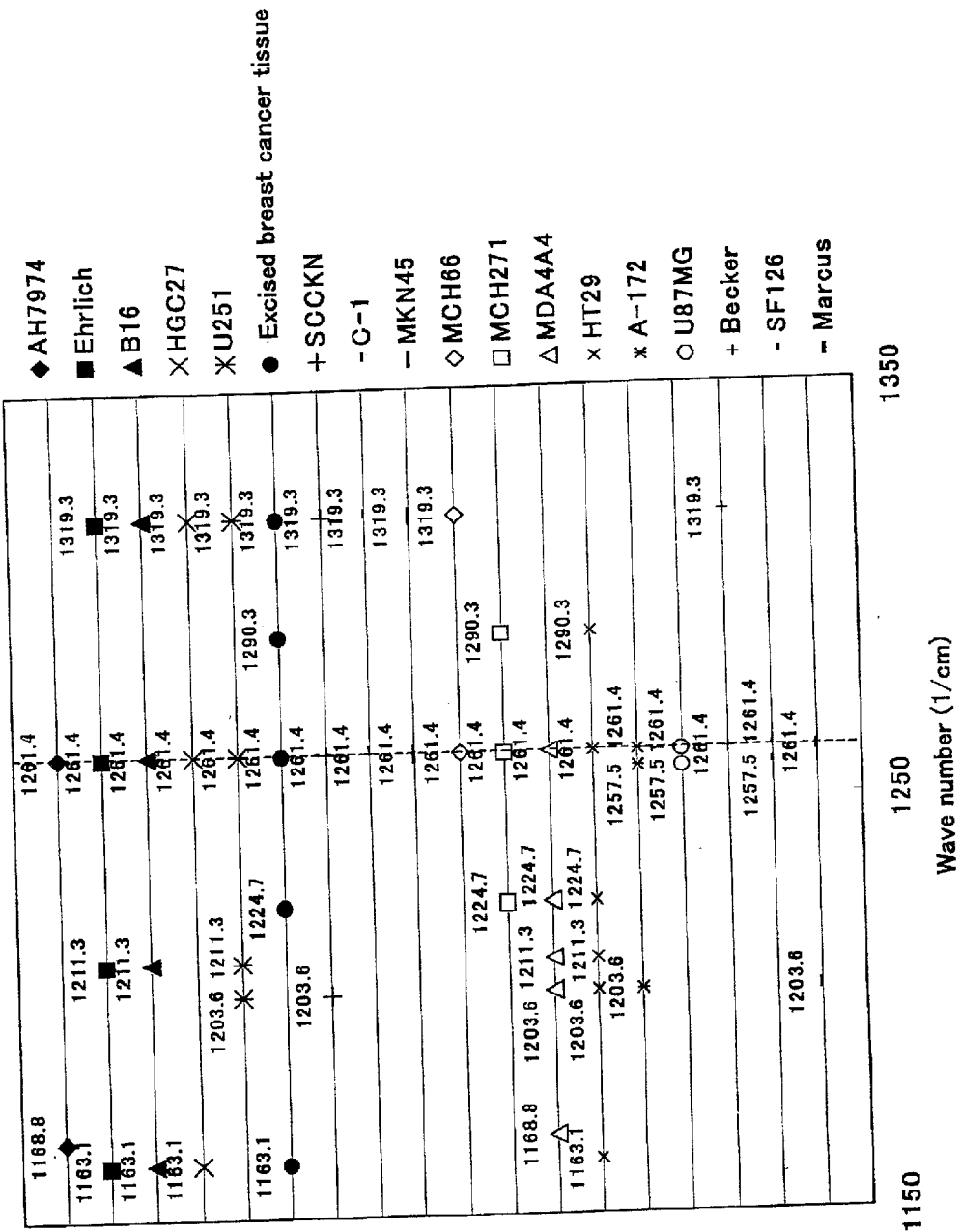
FIG. 8 is a diagram providing a systematic representation of the peak wave numbers of the infrared absorption spectra of various cancer cells.

FIG. 8 is a diagram providing a systematic representation of the peak wave numbers of the infrared absorption spectra of various cancer cells.

FIG. 8 shows the data resulting from adding 12 types of cancer cell samples to each of the samples shown in the above FIGS. 2 through 7. More specifically, cultured cells derived from human tongue cancer (SCCKN), cultured cells derived from human colon cancer (C-1), cultured cells derived from human stomach cancer (MKN45), cultured cells derived from mouse breast cancer (MCH66, MCH271), cultured cells derived from human breast cancer (MDA4A4), cultured cells derived from human colon cancer (HT29), and cultured cells derived from human glioblastoma (A-172, U87MG, Becker, SF126, Marcus) were respectively added as samples.

As shown in FIG. 8, it was found that there was a wave number of 1261.4 cm$^{-1}$ that was common to the characteristic absorption spectrum of each type of cancer cell, and there were also characteristic absorption spectra that were common to not all but some of the cancer cells. Namely, the cancer cells were thought to have absorption spectra corresponding to at least two wave numbers with respect to the infrared region. Within the range of the measurement results shown, those wave numbers of infrared absorption spectra that were able to be judged to be specific for cancer cells consisted of 1261.4 cm$^{-1}$ as well as 1163.1 cm$^{-1}$, 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$. It should be noted that the infrared absorption spectra specific to cancer cells are not limited to the above wave numbers.

Moreover, the following provides a detailed explanation of what is meant by the energy state characteristic of cancer cells as described above being a metastable state.

In order to show that this energy state is a metastable state, measurements were performed here to determine the manner in which the energy state of the system changes as a result of disturbing the system with respect to the cancer cells, namely destroying the cell membrane.

Figure 9:
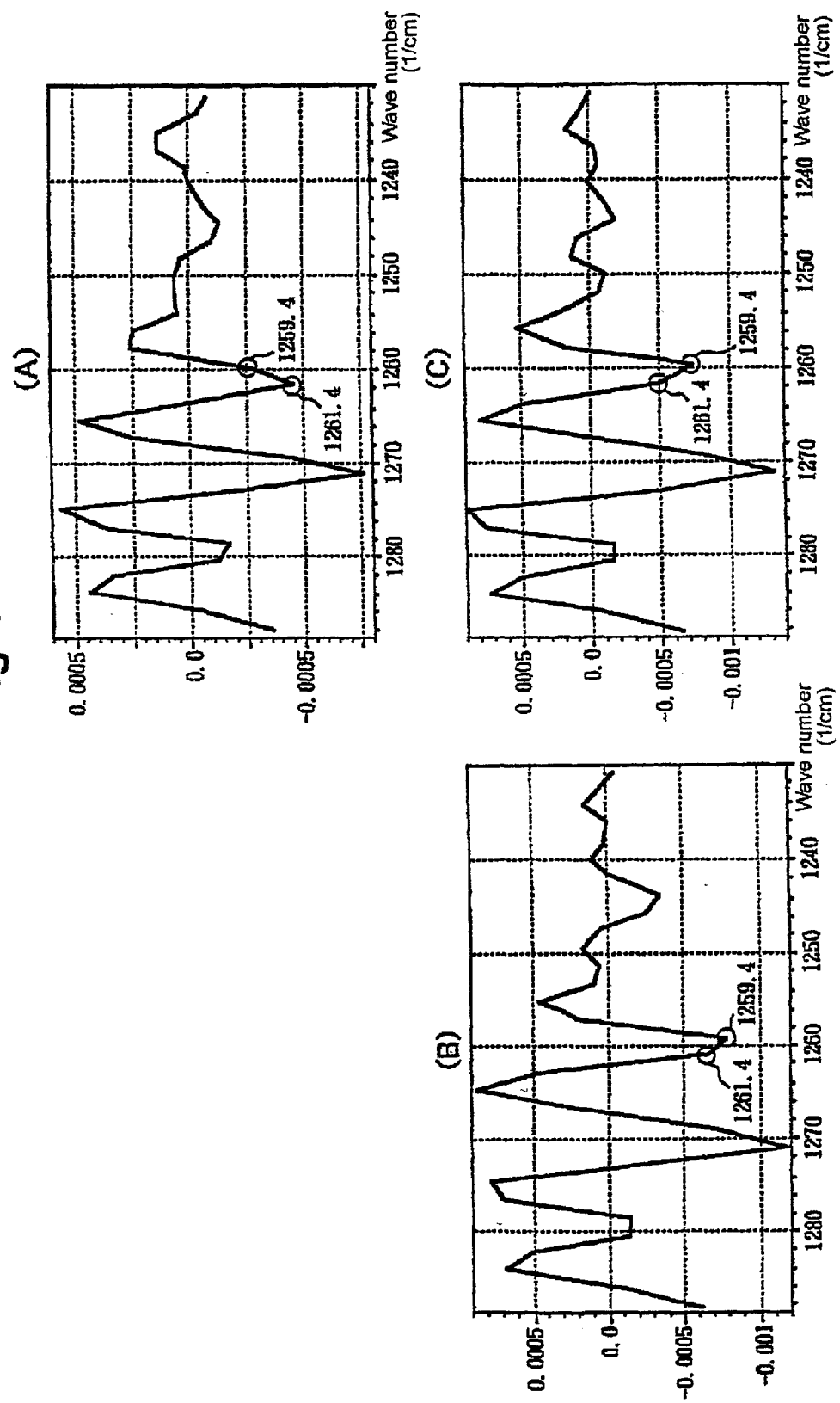
FIGS. 9A, 9B, and 9C show graphs illustrating changes in energy states caused by destruction of the cell membrane of cancer cells.

FIG. 9 shows graphs illustrating changes in energy states caused by destruction of the cell membrane of cancer cells. (A) indicates the secondary differential data of the infrared absorption spectrum measured immediately after destruction, (B) indicates the secondary differential data two minutes after destruction, and (C) indicates the secondary differential data 5 minutes after destruction.

As shown in FIG. 9, the absorption spectrum at a wave number of 1261.4 cm$^{-1}$ characteristic of cancer cells rapidly changes to an absorption spectrum having a wave number of 1259.4 cm$^{-1}$ due to destruction of the cell membrane. This transition of the absorption spectrum indicates a change from energy state Em to energy state Em* (Em>Em*), and ultimately ends after reaching a state of Em* alone after going through a state in which both energy states Em and Em* are present. The amount of time required to change from energy state Em to energy state Em* after going through a state of coexistence of both energy states is dependent upon the type of cancer cells and environmental temperature, and it is generally considered to be about 10 to 300 seconds.

In addition, measurements were also made to determine the manner in which the energy state of the system changes as a result of heating (43° C.) without destroying the cell membrane with respect to cancer cells.

Figure 10:
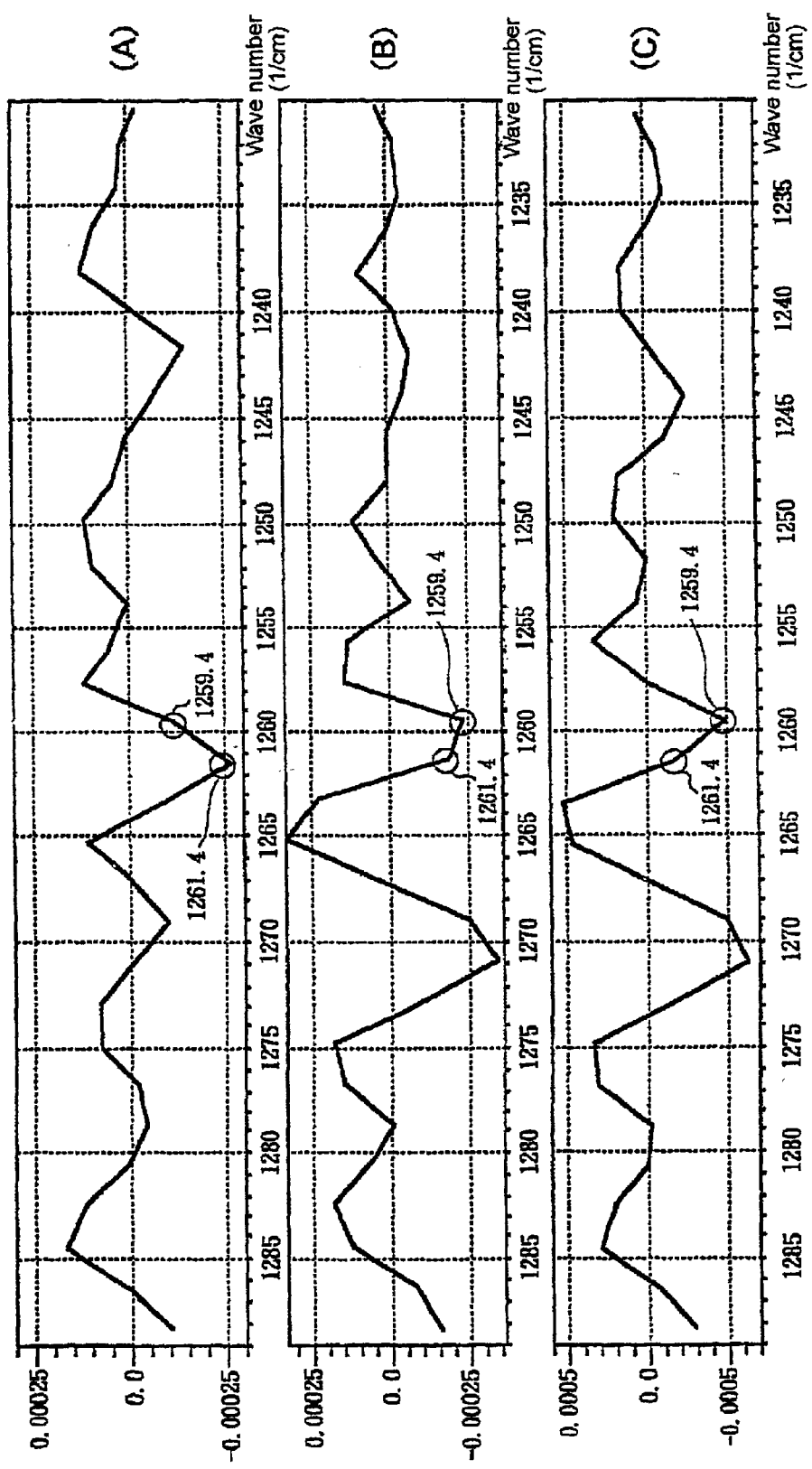
FIGS. 10A, 10B, and 10C show graphs illustrating changes in energy states caused by heating cancer cells.

FIG. 10 shows graphs illustrating changes in energy states caused by heating cancer cells. (A) indicates the secondary differential data of the infrared absorption spectrum measured before heating, (B) indicates the secondary differential data immediately after heating for 30 minutes, and (C) indicates the secondary differential data 30 minutes after heating.

As shown in FIG. 10, it was found that the absorption spectrum having a wave number of 1261.4 cm$^{-1}$ changes to a wave number of 1259.4 cm$^{-1}$ due to heating the cancer cells, and that the energy state changes from Em to Em*.

In this manner, based on the fact that the energy state Em characteristic of cancer cells changes to another energy state Em* as a result of changing the energy state of the system by destroying the cell membrane or heating cancer cells, energy state Em can be considered to be a metastable state.

Secondly, it is also necessary to confirm that an energy level characteristic of cancer cells is not present in normal cells.

In order to confirm the above fact, infrared absorption spectra were measured using FT-IR in the same manner as in the previous case using 30 types of normal cells including rat and mouse normal cells and normal human bone marrow cells.

FIGS. 11 through 14 are graphs shown examples of the results of spectral analysis performed on various types of normal cells. However, (A) in each figure indicates the infrared absorption spectrum as measured by FT-IR, while (B) indicates the results of second order differentiation processing of the data of (A).

More specifically, FIG. 11 indicates data in the case of using as a sample normal rat brain (white matter) cells, FIG. 12 indicates that of normal rat liver cells, FIG. 13 indicates that of normal mouse mammary gland cells, and FIG. 14 indicates that of normal human bone marrow cells.

As shown in FIGS. 11 through 14, it is found that a spectrum that strictly coincides (within the range of a measuring accuracy of ±0.1 cm$^{-1}$) with the infrared absorption spectrum measured for the cancer cells is not present for the normal cells. Thus, it can be judged that the previously mentioned wave number of 1261.4 cm$^{-1}$ and the other infrared absorption spectra are specific for cancer cells.

Figure 15:
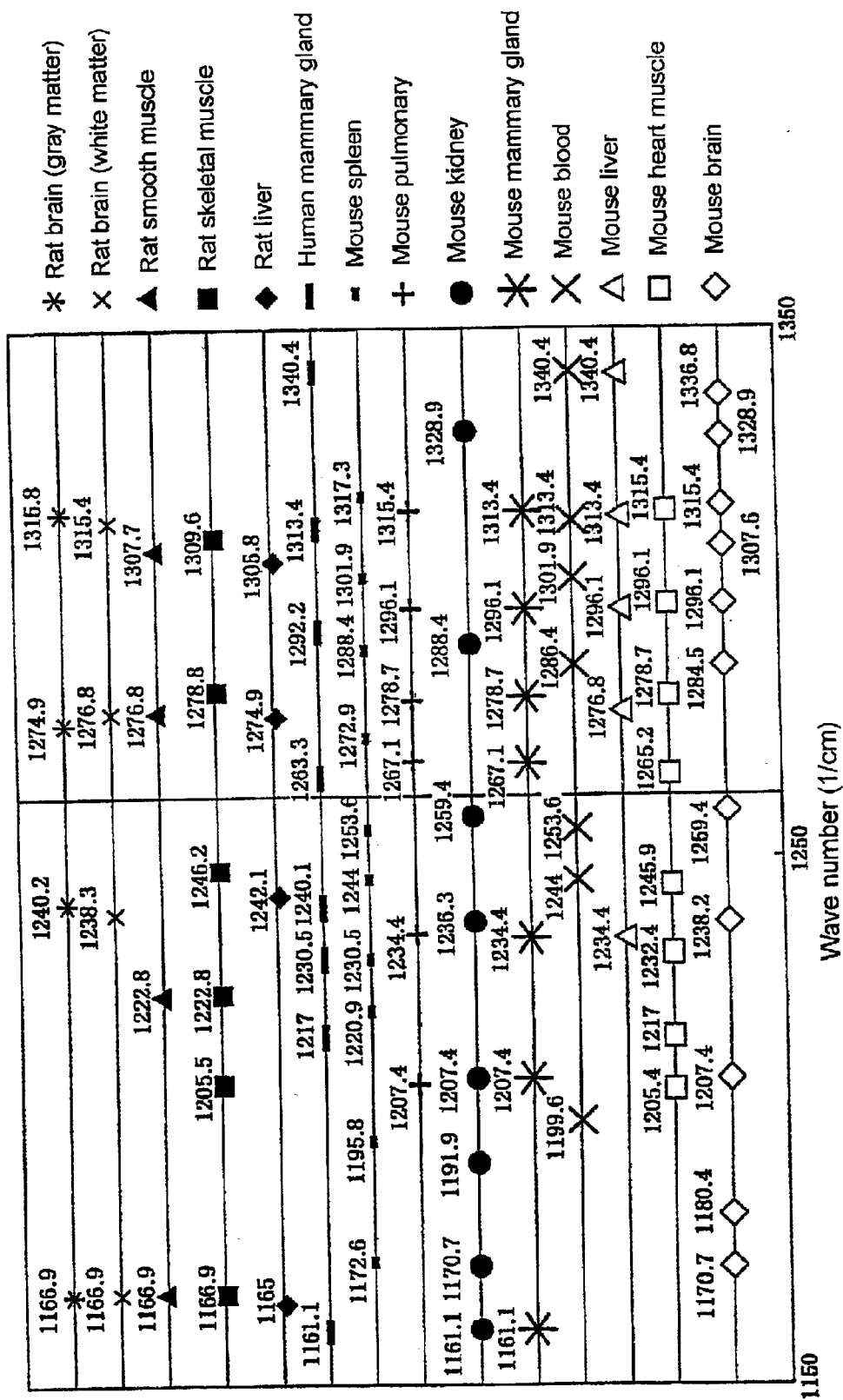
FIG. 15 is a diagram providing a systematic representation of the peak wave numbers of the infrared absorption spectra of normal cells.

Furthermore, it was unknown at the time of filing of the present application as to whether or not a common absorption spectrum exists for all normal cells as in the case of cancer cells. FIG. 15 is a diagram providing a systematic representation of the peak wave numbers of the infrared absorption spectra for some of the 30 types of normal cells measured.

Thirdly, it is necessary to confirm that an energy level that coincides with the energy level characteristic of cancer cells is present in anti-cancer agents.

In order to confirm the above fact, measurements of infrared absorption spectra were performed using FT-IR and various types of typical anti-cancer agents as samples. It should be noted that all of the samples used were physiological saline solutions of the pure drugs.

FIGS. 16 through 19 are graphs illustrating examples of the results of performing spectral analysis of various anti-cancer agents. However, (A) in each figure indicates the infrared absorption spectrum measured by FT-IR, while (B) indicates the results of second order differentiation processing of the data of (A).

More specifically, FIG. 16 indicates the data in the case of using cisplatin for the sample, FIG. 17 indicates the use of carboplatin, FIG. 18 indicates the use of doxorubicin hydrochloride (drug name: Adriacin, (Kyowa Hakko)), and FIG. 19 indicates the use of nimustine hydrochloride (ACNU).

Each of the anti-cancer agents shown in FIGS. 16 through 19 has an absorption peak at a wave number of 1261.4 cm$^{-1}$, and this strictly coincides with the absorption spectrum characteristic of cancer cells. In addition, cisplatin and doxorubicin hydrochloride also have an absorption spectrum at a wave number of 1163.1 cm$^{-1}$, while ACNU has an absorption spectrum at wave numbers of 1203.6 cm$^{-1}$ and 1211.3 cm$^{-1}$. These also strictly coincides with the absorption spectrum characteristic of cancer cells. Although the specific spectrum analysis results have been omitted from the graphs, in addition to those mentioned above, anti-cancer agents having an absorption spectrum at a wave number of 1163.1 cm$^{-1}$ included fluorouracil (drug name: 5-FU (Kyowa Hakko)), methotrexate (MTX) and bleomycin hydrochloride (BLM). Moreover, an absorption spectrum at a wave number of 1261.4 cm$^{-1}$ was also confirmed for both CBDCA, a variation of cisplatin, and Epi-ADR, a variation of doxorubicin hydrochloride.

In general, each of the anti-cancer agents shown in FIGS. 16 through 19 are anti-cancer agents having powerful killing damaging effects that are the first choice in cancer chemotherapy. On the other hand, fluorouracil, methotrexate and bleomycin hydrochloride are anti-cancer agents having comparatively mild action. Thus, it is believed that the sharing of an absorption spectrum at a wave number of 1261.4 cm$^{-1}$ with cancer cells is a required condition for being a powerful anti-cancer agent. However, since it is also a fact that there are numerous cancer cells for which anti-cancer agents having an absorption spectrum at a wave number of 1261.4 cm$^{-1}$ are completely ineffective, it is clear that the having of an absorption spectrum at a wave number of 1261.4 cm$^{-1}$ cannot be a sufficient condition for being a powerful anti-cancer agent. This is thought to be because the above-mentioned cancer cells are allowed to adopt a plurality of states in addition to the energy state corresponding to an absorption spectrum at a wave number of 1261.4 cm$^{-1}$.

Fourthly, it is necessary to confirm that an intrinsic energy level exists between anti-cancer agents and normal cells damaged by adverse side effects.

In order to confirm the above fact, an experiment was conducted here focusing on the myocardial toxicity of, for example, doxorubicin hydrochloride (Adriacin). More specifically, a wave number of 1217.0 cm$^{-1}$ was identified as an infrared absorption spectrum that coincides between doxorubicin hydrochloride and mouse heart muscle. In order for this absorption spectrum to be the cause of myocardial toxicity, it is necessary that this absorption spectrum be intrinsic to heart muscle, and that an absorption spectrum at a wave number of 1217.0 cm$^{-1}$ not be present in epirubicin hydrochloride (drug name: Farmorubicin (Farmitalia-Kyowa Hakko)), in which the adverse side effect of myocardial toxicity has been removed, or other anti-cancer agents which do not inherently possess myocardial toxicity. Therefore, the infrared absorption spectra were measured using doxorubicin hydrochloride, epirubicin hydrochloride, cisplatin, carboplatin, ACNU, mouse heart muscle, striated muscle and smooth muscle as samples.

FIGS. 20 through 24 are graphs showing examples of secondary differential data of the infrared absorption spectra measured for each of the above samples.

Figure 20:
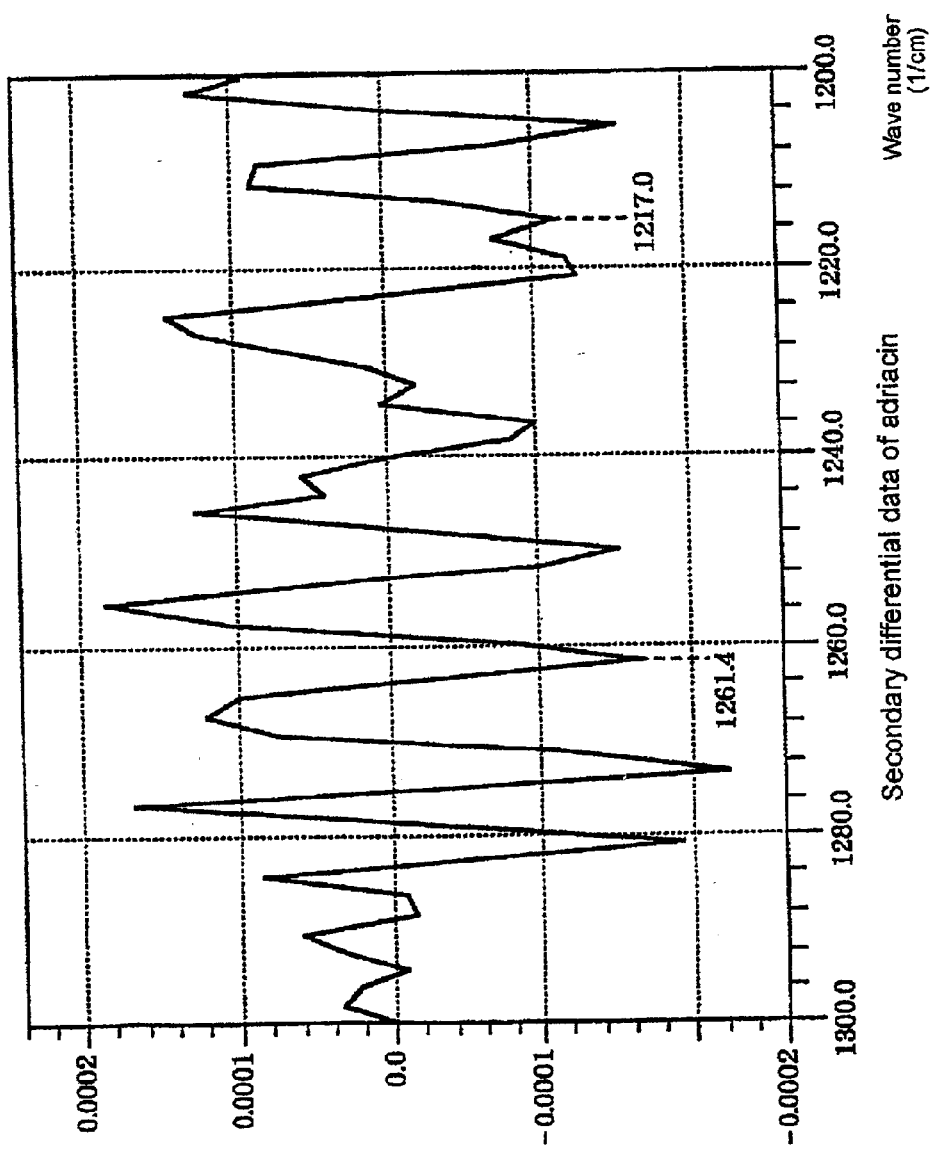
FIG. 20 is a graph illustrating secondary differential data of the infrared absorption spectrum of doxorubicin hydrochloride (Adriacin).
Figure 21:
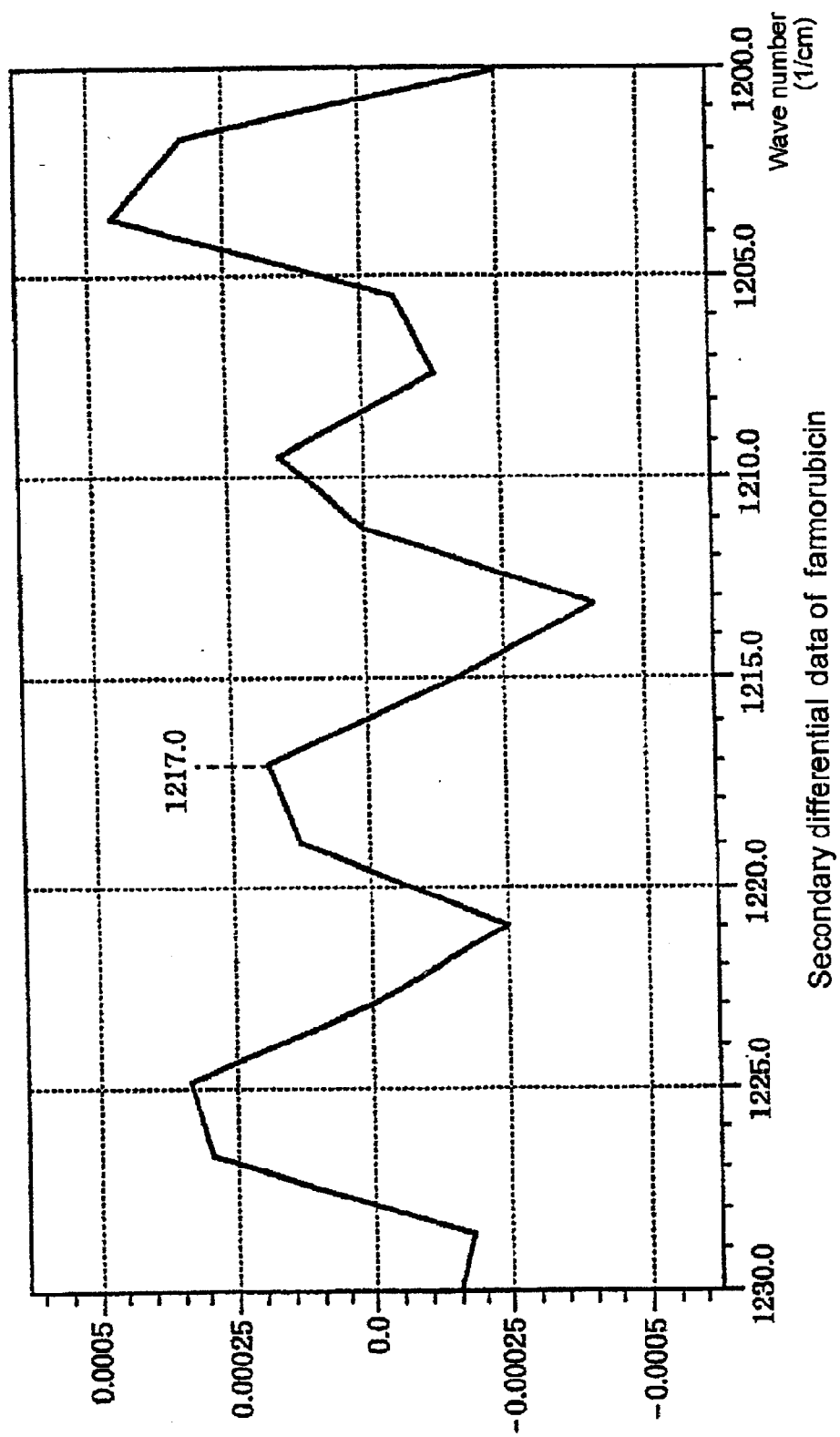
FIG. 21 is a graph illustrating secondary differential data of the infrared absorption spectrum of nimustine hydrochloride (ACNU).
Figure 22:
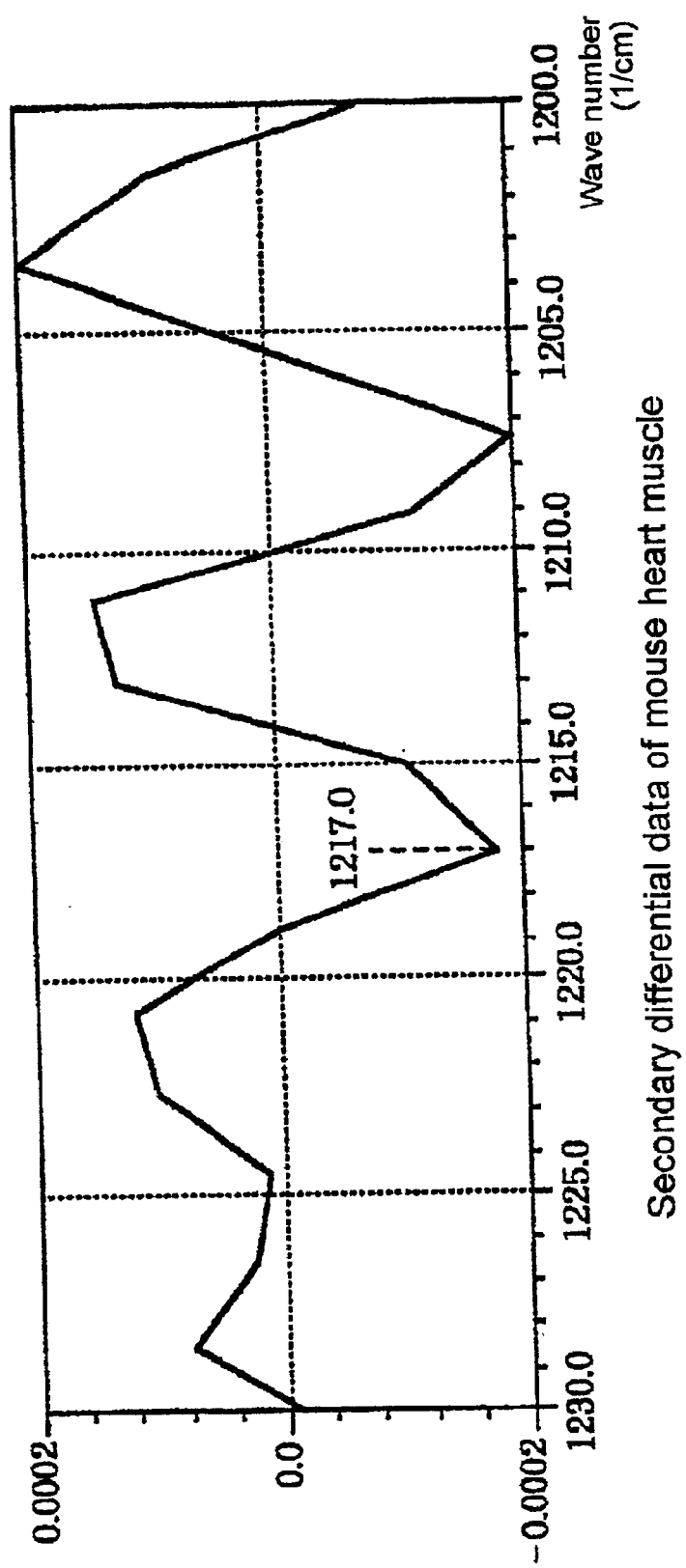
FIG. 22 is a graph illustrating secondary differential data of the infrared absorption spectrum of mouse heart muscle.
Figure 23:
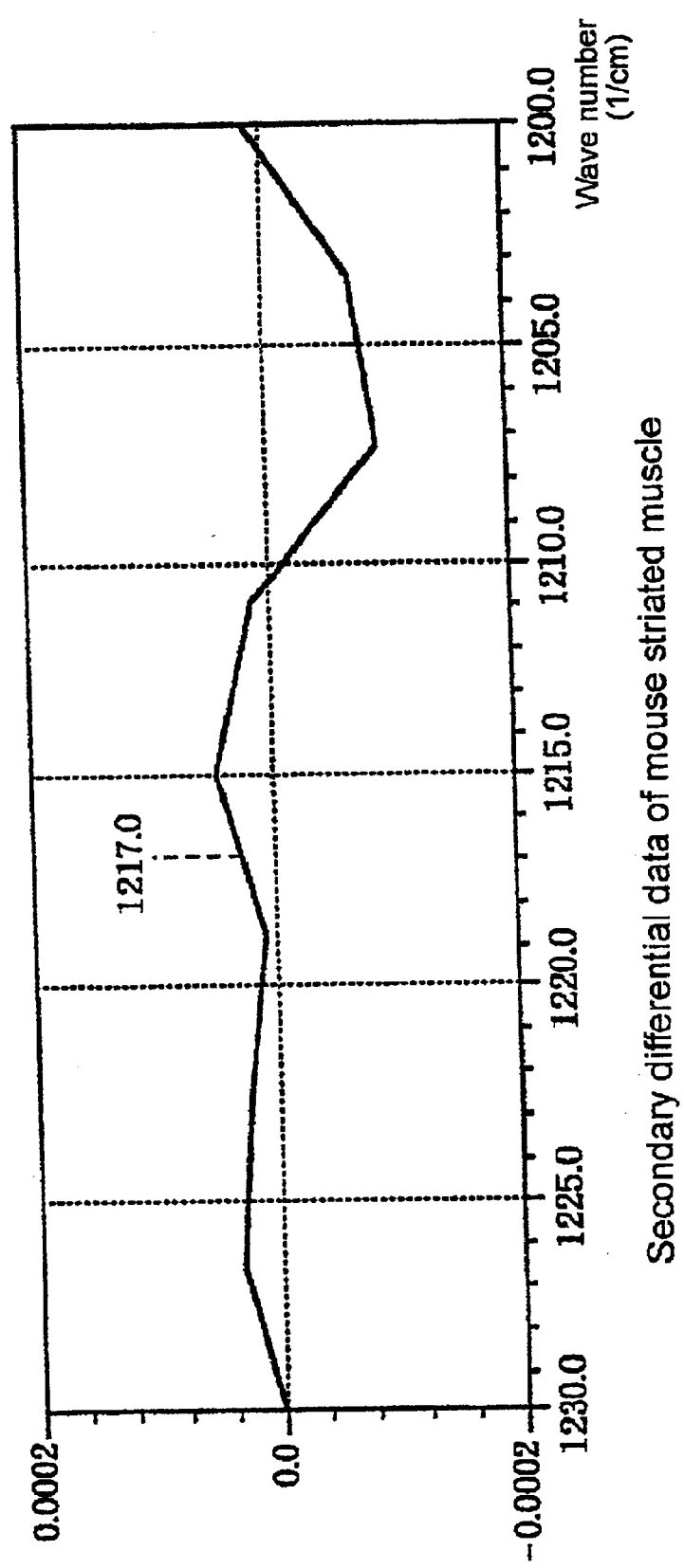
FIG. 23 is a graph illustrating secondary differential data of the infrared absorption spectrum of mouse striated muscle.
Figure 24:
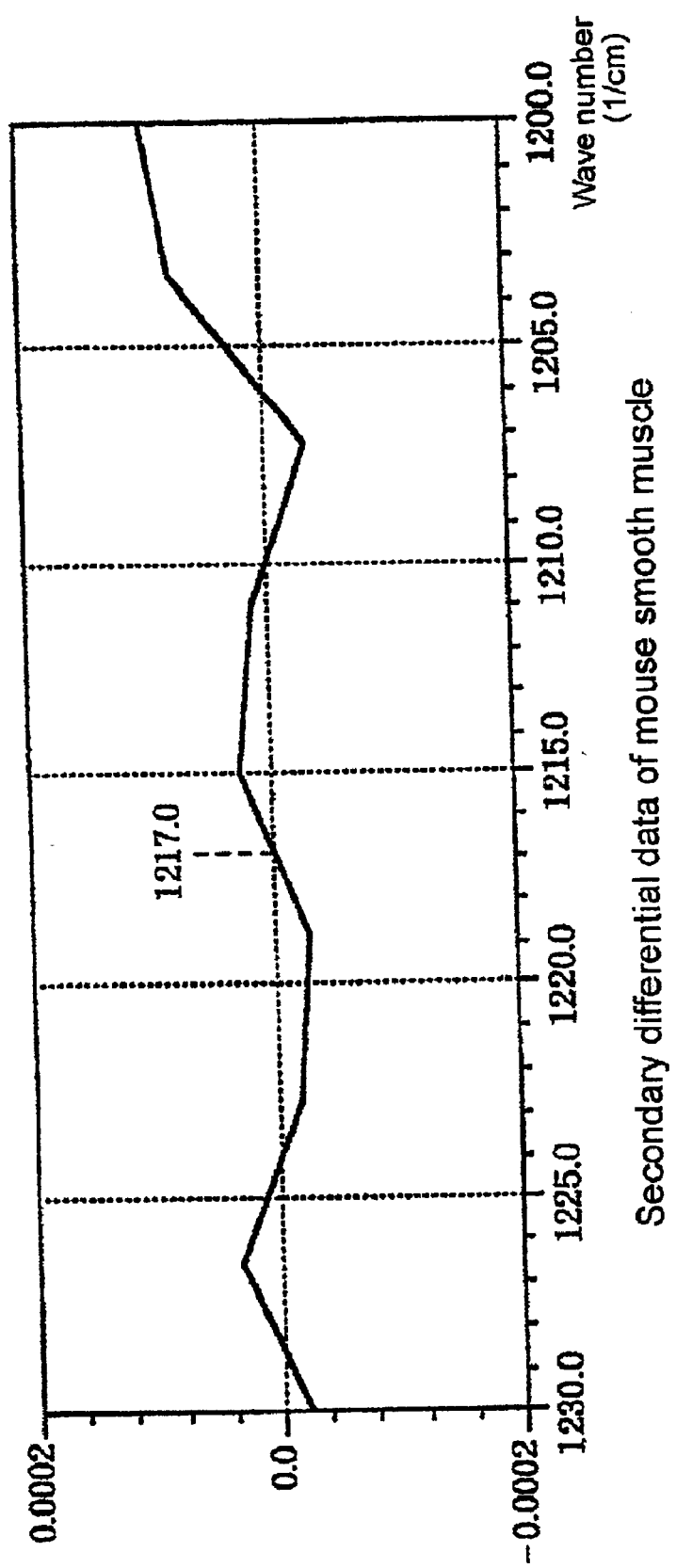
FIG. 24 is a graph illustrating secondary differential data of the infrared absorption spectrum of mouse smooth muscle.

More specifically, FIG. 20 shows the secondary differential data in the case of using doxorubicin hydrochloride for the sample, FIG. 21 shows that in the case of using epirubicin hydrochloride, FIG. 22 shows that in the case of using mouse heart muscle, FIG. 23 shows that in the case of using mouse striated muscle, and FIG. 24 shows that in the case of using smooth muscle.

As shown in FIGS. 20 through 24, the absorption spectrum at a wave number of 1217.0 cm$^{-1}$ is clearly a spectrum intrinsic only to doxorubicin hydrochloride and heart muscle, and the above findings were strictly confirmed experimentally.

As a result of being able to confirm the first to fourth facts described above, it can be judged that it is reasonable to think that absolute specificity regarding cancer cells or anti-cancer agents relative to normal cells is observed in the form of differences in the energy states of the systems.

The explanation thus far has focused on the specificity possessed by cancer cells and anti-cancer agents, and the above approach can be similarly applied to bacteria and antibiotics as well as to viruses and anti-viral agents. This is because ordinary cells, including cells that have been infected by bacteria and viruses, are an open system that is in a state of thermal imbalance with respect to their survival, and the normal state (energy state En shown in the above FIG. 1) is also not considered to be a basal state, but rather an unstable excited state, namely a metastable state. This is clear from the fact that the situation in which normal cells require a supply of energy from the outside in order to demonstrate biological activity is not different from that of cancer cells.

In order to confirm the above contents experimentally, measurement of infrared absorption spectrum was performed by FT-IR using *Escherichia coli* and aztreonam (drug name: Azactam, Eisai), which is known to be an effective antibiotic against it, as samples.

FIG. 25 shows graphs illustrating the results of infrared spectral analysis in the case of using *Escherichia coli* as a sample, while FIG. 26 shows graphs illustrating the results of spectral analysis in the case of using aztreonam (Azactam) as a sample. However, (A) in each figure indicates the infrared absorption spectrum measured by FT-IR, while (B) indicates the results of second order differentiation processing of the data of (A).

As shown in FIGS. 25 and 26, an absorption peak at a wave number of 1259.4 cm$^{-1}$ was identified as an infrared absorption spectrum common to *Escherichia coli* and aztreonam. Moreover, this absorption spectrum having a wave number of 1259.4 cm$^{-1}$ is also present in cisplatin (FIG. 16) and carboplatin (FIG. 17) previously mentioned as anti-cancer agents. This can be considered to suggest the possibility that cisplatin and carboplatin also have the ability to impair *Escherichia coli*.

In addition, the infrared absorption spectrum was also measured for transplatin, a coordination isomer of cisplatin.

FIG. 27 shows graphs illustrating the results of spectral analysis in the case of using transplatin as a sample, and (A) indicates the measured infrared absorption spectrum, while (B) indicates the secondary differential data.

As shown in FIG. 27, although transplatin has an absorption spectrum at a wave number of 1259.4 cm$^{-1}$ that is common to *Escherichia coli*, it can be seen that there are no spectra that coincide with the characteristic absorption spectrum of cancer cells. This is believed to suggest the possibility that even though transplatin is a coordination isomer of cisplatin, it has the ability to impair *Escherichia coli* but does not have the ability to impair cancer cells.

Moreover, an attempt was also made to measure the infrared absorption spectra for samples consisting of the drug resistance bacteria, methicillin-resistant *Staphylococcus aureus* (MRSA), *Staphylococcus aureus* (SA), the origin of the MRSA, and vancomycin (VM), an antibiotic that is effective against both MRSA and *Staphylococcus aureus*.

The following Table 1 shows the absorption peak wave numbers of the infrared absorption spectra measured for each of these samples.

TABLE 1

| MRSA | S.A. | V.M. |
|---|---|---|
| 1006.8 | 1006.8 | |
| 1010.6 | | 1014.4 |
| 1022.2 | 1022.2 | 1018.3 |
| 1033.8 | 1033.8 | 1029.9 |
| 1041.5 | 1037.6 | |
| 1056.9 | 1056.9 | 1064.6 |
| 1076.2 | | 1076.2 |
| 1083.9 | 1083.9 | 1080.1 |
| 1087.8 | 1087.8 | |
| 1118.6 | 1118.6 | 1130.2 |
| 1172.6 | 1172.6 | 1176.5 |
| 1195.8 | | 1195.8 |
| 1218.9 | 1218.9 | |
| 1234.4 | | 1234.4 |
| 1242.1 | 1242.1 | |
| 1245.9 | 1245.9 | |
| 1265.2 | | 1265.2 |
| 1280.7 | 1280.7 | |
| | 1296.1 | 1296.1 |
| 1303.8 | 1303.8 | 1311.5 |

As shown in Table 1, absorption spectra were confirmed to coincide between MRSA and vancomycin at wave numbers of 1076.2 cm$^{-1}$, 1195.8 cm$^{-1}$, 1234.4 cm$^{-1}$ and 1265.2 cm$^{-1}$. In addition, an absorption spectrum at a wave number of 1296.1 cm$^{-1}$ was confirmed to coincide between *Staphylococcus aureus* and vancomycin.

In this manner, the approach of observing the absolute specificity of cells as differences in the energy state of the system can be judged to be valid even when applying to bacteria such as *Escherichia coli*, MRSA and *Staphylococcus aureus* as well as antibiotics that act on said bacteria.

In addition, although the experimental results shown thus far have focused on drugs that impair cancer cells and *Escherichia coli*, the fact has also been confirmed that coincidence between the infrared absorption spectra of cells and drugs activates cell growth.

Here, the infrared absorption spectra were measured for samples consisting of, for example, lenograstim (drug name: Neutrogin, Chugai Pharmaceutical), filgrastim (drug name: Gran, Sankyo) and normal human bone marrow cells. Furthermore, lenograstim and filgrastim are both drugs that increase leukocytes and are used during bone marrow transplants, with lenograstim being a drug that is extracted from the ovaries of Chinese hamsters, and filgrastim being a drug that is synthesized in *Escherichia coli* that has a different molecular structure than lenograstim.

Figure 28:
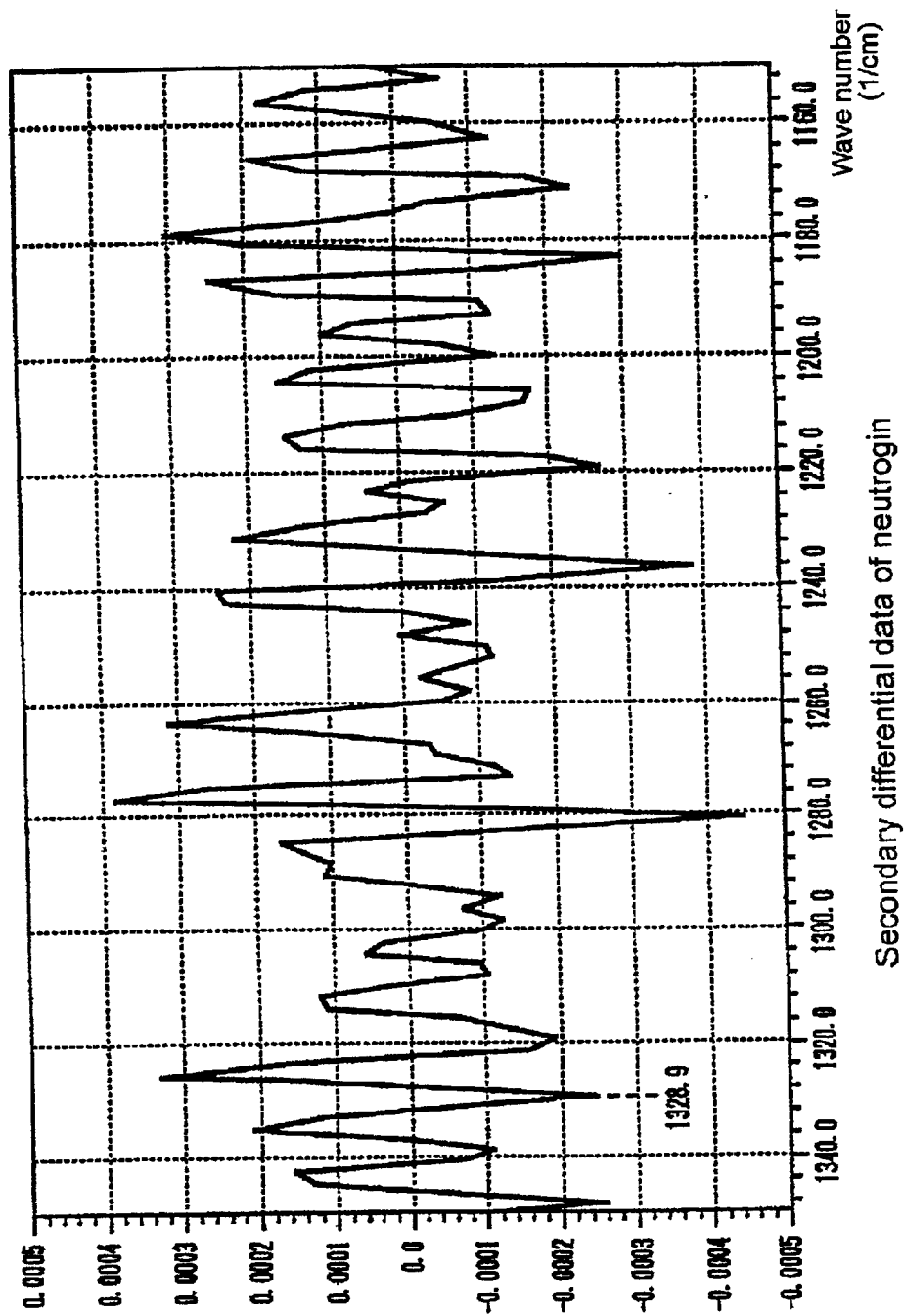
FIG. 28 is a graph showing the secondary differential data of the infrared absorption spectrum of lenograstim (Neutrogin).
Figure 29:
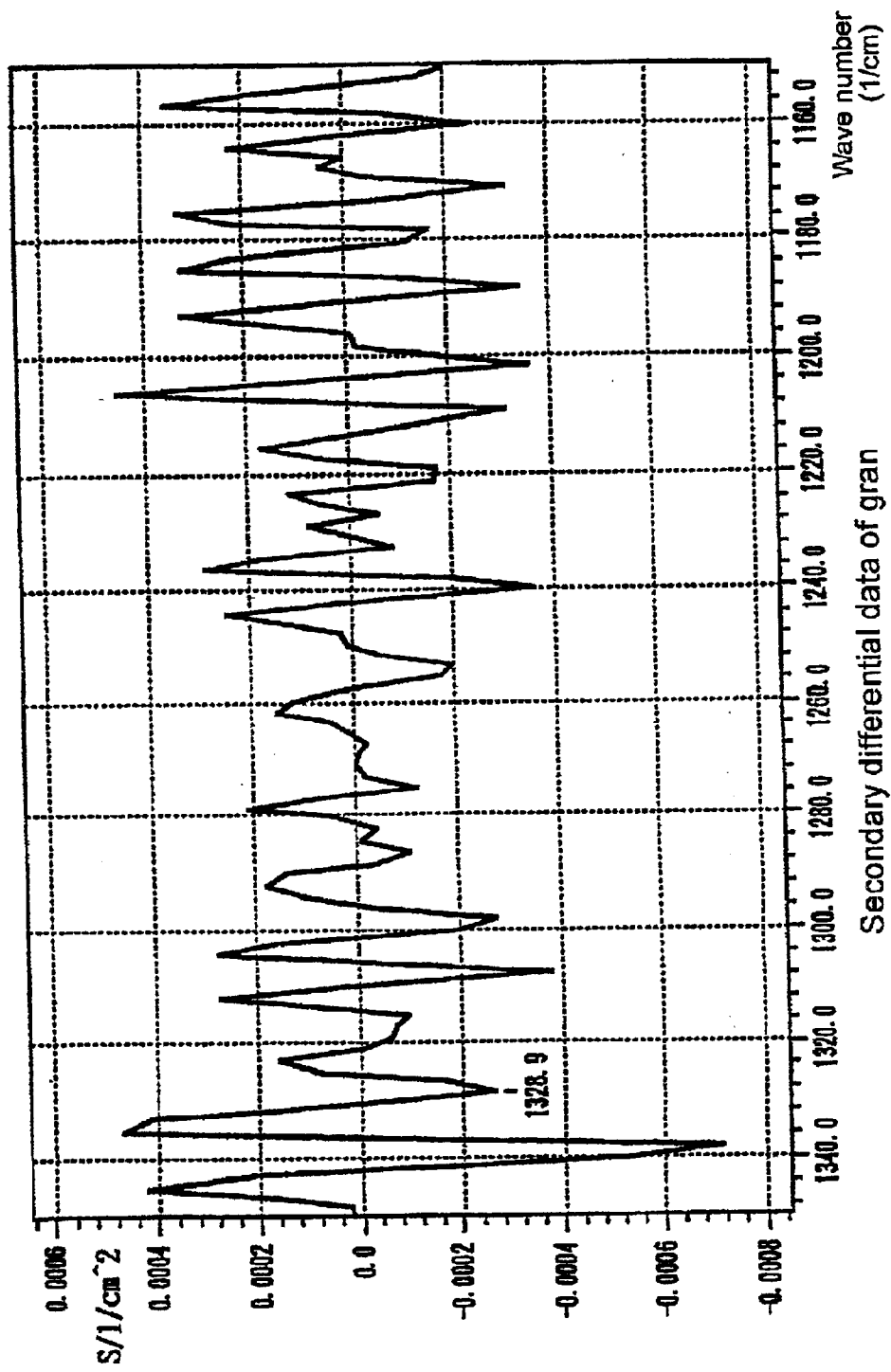
FIG. 29 is a graph showing the secondary differential data of the infrared absorption spectrum of filgrastim (Gran).
Figure 30:
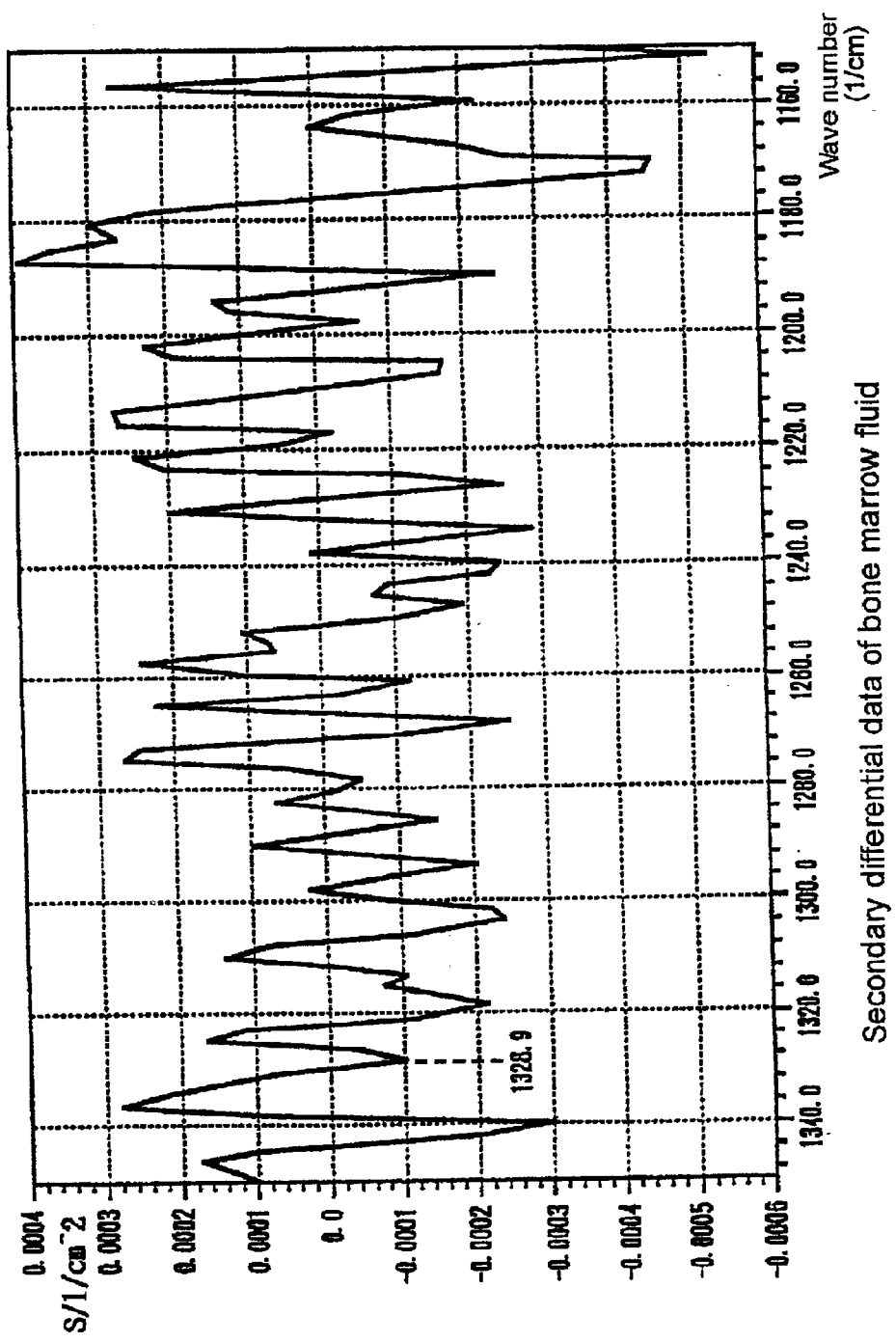
FIG. 30 is a graph showing the secondary differential data of the infrared absorption spectrum of human bone marrow fluid.

FIGS. 28 through 30 show the secondary differential data of the infrared absorption spectra measured for each of the above samples, with FIG. 28 showing the data for lenograstim, FIG. 29 showing that for filgrastim, and FIG. 30 showing that for bone marrow fluid.

As shown in FIGS. 28 through 30, the absorption spectra of lenograstim, filgrastim and bone marrow fluid can be seen to strictly coincide at a wave number of 1328.9 cm$^{-1}$. In this manner, coincidence between the absorption spectra of cells and drugs is thought to be effective with respect to the case of activation of cell growth as well.

Next, in order to experimentally confirm that the approach of the present invention can also be applied to viruses and anti-viral agents, the infrared absorption spectra were measured by FT-IR for samples consisting of, for example, KOS virus, which is a type of herpes virus that has drug sensitivity, and aciclovir (drug name: Zovirax, Sumitomo-Welcam Japan), which is known to be an effective anti-viral agent against the KOS virus.

Here, fibroblasts (VERO cells) and kidney cells of rhesus monkeys (MRC5 cells) were used as cells infected with the above KOS virus and in which the KOS virus was allowed to grow. The infrared absorption spectra were then measured for each of the sample cells before viral infection and 1, 3 and 5 days after infection. In addition, the infrared absorption spectrum of the anti-viral agent aciclovir was also measured.

The following Table 2 shows the absorption peak wave numbers of the infrared absorption spectra measured for each sample.

TABLE 2

| VERO (cm$^{-1}$) | | | | MRC5 (cm$^{-1}$) | | | | |
|---|---|---|---|---|---|---|---|---|
| Before infection | One day after infection | Three days after infection | Five days after infection | Before infection | One day after infection | Three days after infection | Five days after infection | Aciclovir (cm$^{-1}$) |
| | | | | | | | | 1010.6 |
| | | 1016.4 | 1016.4 | | | 1016.4 | | |
| | 1022.2 | | | | 1022.2 | | | |
| | | | | | | | | 1029.9 |
| 1037.6 | | | | 1037.6 | 1037.6 | | | |
| | | 1041.5 | 1041.5 | | | | | |
| | | | | | | | | 1047.3 |
| | | 1049.2 | 1049.2 | | | 1049.2 | 1049.2 | |
| | | | 1051.1 | | | 1051.1 | | |
| 1055.0 | | | | 1055.0 | 1055.0 | | | |
| | | 1058.8 | 1058.8 | | | 1058.8 | 1058.8 | |
| | | 1064.6 | 1064.6 | | | 1064.6 | 1064.6 | |
| 1068.5 | | | | 1068.5 | 1068.5 | | | |
| | | | | | | | | 1071.4 |
| | | | | | | | | 1083.0 |
| | | 1087.8 | 1087.8 | | | 1087.8 | 1087.8 | |
| | | | | | | | | 1091.6 |
| 1103.2 | | | | 1103.2 | 1103.2 | | | |
| | 1105.1 | 1105.1 | 1105.1 | | | 1105.1 | | 1105.1 |
| | | 1107.1 | 1107.1 | | | 1107.1 | 1107.1 | |
| | | | | | | | | 1117.7 |
| | | 1122.5 | 1122.5 | | | | 1122.5 | 1122.5 |
| | | 1157.2 | 1157.2 | | | 1157.2 | | |
| | 1161.1 | | | | 1161.1 | | | |
| | | | 1176.5 | | 1176.5 | | 1176.5 | |
| | | | | | | | | 1179.4 |
| | 1182.3 | 1182.3 | 1182.3 | | | 1182.3 | | |
| | 1193.9 | 1193.9 | 1193.9 | | 1193.9 | | | |
| | | 1195.8 | 1195.8 | | 1195.8 | | 1195.8 | |
| | 1201.6 | | | | 1201.6 | | | |
| | | 1207.4 | 1207.4 | | | 1207.4 | | |
| 1209.3 | | | | 1209.3 | 1209.3 | | | |
| | | | | | | | | 1213.1 |
| | 1230.5 | | | | 1230.5 | | | |
| 1232.4 | | | | 1232.4 | 1232.4 | | | |
| | | | | | | | | 1233.4 |
| | | 1240.1 | 1240.1 | | 1240.1 | 1240.1 | | |
| | | | | | | | | 1245.0 |
| | | | 1251.7 | | | 1251.7 | | |
| | 1259.4 | 1259.4 | 1259.4 | | 1259.4 | 1259.4 | | |
| | | | | | | | | 1265.2 |
| | | 1269.1 | 1269.1 | | | 1269.1 | 1269.1 | |
| 1274.9 | 1274.9 | | | | 1274.9 | | | |
| | | | | | | | | 1276.8 |
| | | 1278.7 | 1278.7 | | 1278.7 | | | |
| | | | | | | | | 1286.4 |

As shown in Table 2, there were numerous absorption spectra that appeared after viral infection but not before infection for each of the sample cells. In addition, there were also absorption spectra that were present before infection but disappeared after infection. More specifically, examples of spectra that disappeared after infection for both sample cells included those at wave numbers of 1037.6 cm$^{-1}$, 1055.0 cm$^{-1}$, 1068.5 cm$^{-1}$, 1103.2 cm$^{-1}$, 1209.3 cm$^{-1}$, 1232.4 cm$^{-1}$ and 1274.9 cm$^{-1}$. The above fact is believed to indicate that the energy state of cells changes as a result of those cells being infected by virus. This change in the cell energy state is also clear from the fact that the infected cells begin virus replication and eventually die. In addition, absorption spectra were able to be confirmed to coincide between absorption spectra that newly appeared after viral infection and the absorption spectrum of the anti-viral agent aciclovir for each of the sample cells at wave numbers of 1105.1 cm$^{-1}$ and 1122.5 cm$^{-1}$.

In this manner, the approach of observing the absolute specificity of cells as difference in the energy state of the system can be judged to also have validity with respect to application to viruses and anti-viral agents.

As a result of employing the basic approach of the present invention as described above, a disease type and/or condition determination method and apparatus, which enable rapid and accurate determination of condition, as well as a drug screening method and apparatus, which enables efficient screening of drugs, can be realized as indicated below.

To begin with, an explanation is provided regarding an embodiment of the disease type and/or condition determination method according to the present invention.

Figure 31:
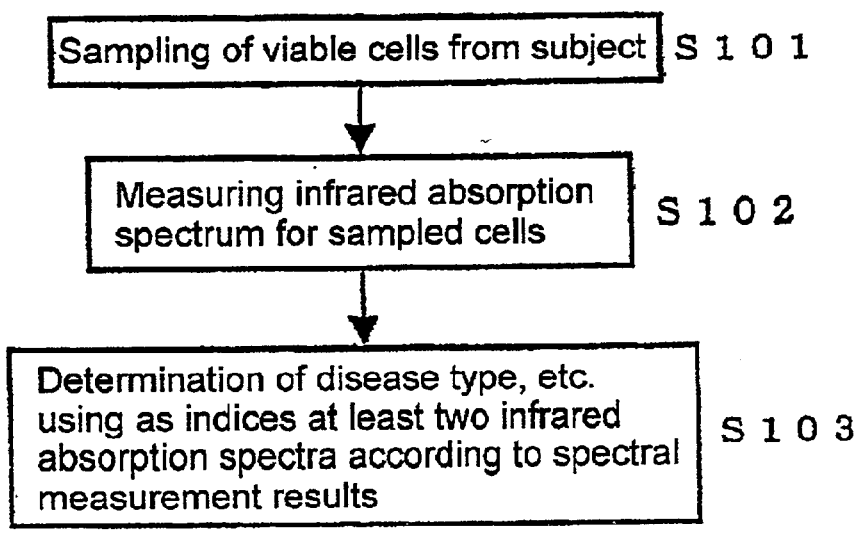
FIG. 31 is a flow chart showing the disease type and/or condition determination method as described in an embodiment of the present invention.

FIG. 31 is a flow chart showing the disease type and/or condition determination method as described in an embodiment of the present invention.

As shown in FIG. 31, in the method of the present embodiment, viable cells are sampled from a specimen in step 101 (indicated as S101 in the figure, and to apply similarly hereinafter), and those cells are then used as a sample.

It should be noted that the specimen from which cells are sampled is not limited to a human, but also applies to a wide range of animals and plants. This is also clear from the experimental data previously described. In addition, the sampled samples may also be cultured and so forth. Moreover, caution is required so that the cells used as a sample do not cause a change in the energy state of the system as a result of destruction of the cell membrane or heating as previously mentioned. More specifically, the sample cells are preferably handled in a low-temperature state.

In step 102, measurement of absorption spectrum is performed in the infrared region by, for example, FT-IR for the viable cells sampled in step 101. Since this measurement is performed in an extremely short period of time, the energy state of the cells can be monitored while the cells are still viable without causing the cells to die.

Next, in step 103, disease type or condition is determined using as an index the appearance of spectra corresponding to at least two wave numbers within the infrared region for the infrared absorption spectrum measured in step 102.

More specifically, in the case cancer is suspected in the specimen, whether or not cancer is present is judged according to whether or not coinciding absorption spectra are present in measurement results by using as an index a plurality of infrared absorption spectra characteristic of cancer cells identified in advance. For the infrared absorption spectra characteristic of cancer cells, that at a wave number of 1261.4 cm$^{-1}$ is essential as previously mentioned, while at least one wave number among 1163.1 cm$^{-1}$, 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$ should also be used as indices (see FIG. 8). In the case an absorption spectrum that coincides with these wave numbers is present in the measurement results, then that specimen is determined to be cancer.

In addition, in the case a specimen is suspected of being infected by, for example, MRSA, the infected state of the specimen is diagnosed by determining whether or not a coinciding absorption spectrum is present in the measurement results using as indices infrared absorption spectra having any of the above wave numbers of 1076.2 cm$^{-1}$, 1195.8 cm$^{-1}$, 1234.4 cm$^{-1}$ and 1265.2 cm$^{-1}$ and so forth.

Moreover, in the case a specimen is suspected of being infected by, for example, KOS virus, the infected state of the specimen is diagnosed by determining whether or not a coinciding absorption spectrum is present in the measurement results using as indices infrared absorption spectra having any of the above wave numbers of 1105.1 cm$^{-1}$ and 1122.5 cm$^{-1}$ and so forth.

It should be noted that although the explanation here has focused on the use of FT-IR having a measuring accuracy of ±0.1 cm$^{-1}$, even in cases of more inferior measuring accuracy, it is still possible to determine disease type and condition, and more specifically, it is thought that a measuring accuracy of about ±1 cm$^{-1}$ should be obtained. Thus, the above values to the right of the decimal point of wave numbers of the absorption spectra used as indices may be rounded up or down as is appropriate. Naturally, it is also possible to use FT-IR having superior measuring accuracy of ±0.1 cm$^{-1}$, and in this case, absorption spectra within the ranges included in the above values should be used as indices.

In addition, as an example of a method for determining the infrared absorption spectra of at least two wave numbers used as indices in order to confirm the presence of a specific bacterium such as MRSA or the presence of a specific virus such as KOS virus, the energy spectra may be analyzed for a specific bacterium or virus and a plurality of other bacteria or viruses followed by determining the presence of that bacterium or virus by identifying specific absorption spectra present in that specific bacterium or virus only.

In this manner, according to the disease type and/or condition determination method of the present embodiment, by employing a simple method involving analyzing the energy spectrum for viable cells obtained from a specimen, the disease type or conditions can be rapidly determined such as whether or not the cells are cancer cells and whether or not the cells are infected by MRSA or KOS virus. In addition, by judging and processing spectral measurement results using as indices the absorption spectra corresponding to a plurality of wave numbers within the infrared region, determination of disease type and so forth can be performed more reliably.

Next, an explanation is provided of an embodiment of a disease type and/or condition diagnostic apparatus according to the present invention.

Figure 32:
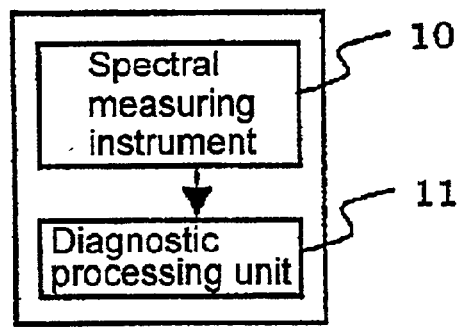
FIG. 32 is a block diagram showing the configuration of a disease type and/or condition diagnostic apparatus as described in an embodiment of the present invention.

FIG. 32 is a block diagram showing the configuration of a disease type and/or condition diagnostic apparatus as described in the present embodiment.

In FIG. 32, the present apparatus 1 is composed of spectral measuring instrument 10, which is used as spectral analysis means that performs analysis of absorption or emission spectra for cells obtained from a specimen, and a diagnostic processing unit 11, which is used as diagnostic means that diagnoses disease type and/or condition based on the measurement results of the spectral measuring instrument 10. Here, an FT-IR system and so forth is used for a spectral measuring instrument 10 that measures absorption spectra for the infrared region. In addition, data relating to infrared absorption spectra used as indices to diagnose disease type and so forth is preset in the diagnostic processing unit 11.

In diagnostic apparatus 1 having the above configuration, viable cells sampled from a specimen are used as a sample, infrared absorption spectrum is measured by the spectral measuring instrument 10, and those measurement results are sent to the diagnostic processing unit 11. In the diagnostic processing unit 11, disease type and condition are diagnosed using as indices the appearance of spectra corresponding to at least two wave numbers in the infrared region for the infrared absorption spectrum measured with the spectral measuring instrument 10 in the same manner as the above-mentioned step 103.

Thus, according to the present embodiment, a diagnostic apparatus can be realized with a simple apparatus configuration that allows rapid and accurate diagnosis of disease type and condition.

It should be noted that although the explanation of each of the above embodiments focused on determining whether or not a specimen has a disease, the present invention is not limited to this application, but is also able to determine the degree of the progress of a disease. As a specific example of this, since the infrared absorption spectrum specific for cancer cells is thought to change depending on metastasis of the cancer and so forth, if spectral wave numbers used as indices are suitably set by correlating with the site of the cancer and so forth, and spectral analysis is performed on extracted cells, then the degree of the progress of that cancer can be determined. In addition, this can also be applied similarly to bacterial and viral infections.

Next, an explanation is provided of an embodiment of the drug screening method according to the present invention.

Figure 33:
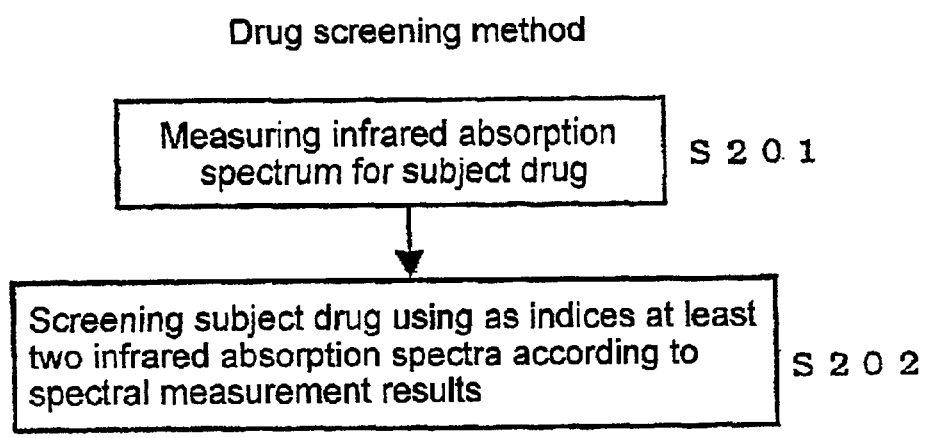
FIG. 33 is a flow chart showing the drug screening method as described in an embodiment of the present invention.

FIG. 33 is a flow chart showing the drug screening method as described in the present embodiment.

In the drug development method shown in FIG. 33, the absorption spectrum in the infrared region is measured using, for example, FT-IR for a new drug or existing drug for which new action (including adverse side effects) is expected (target drug) in step 201.

Next, in step 202, the target drug is screened using as indices the appearance of spectra corresponding to at least two wave numbers in the infrared region for the infrared absorption spectrum measured in step 201.

More specifically, in the case the target drug is, for example, an anti-cancer agent, screening is performed on the condition that there is at least one coinciding absorption spectrum in the spectral measurement results of the target drug among the plurality of infrared absorption spectrum used as indices at wave numbers of 1261.4 cm$^{-1}$, 1163.1 cm$^{-1}$ and so forth as previously mentioned. Moreover, if an anti-cancer agent is to be selected that does not have the adverse side effect of myocardial toxicity, for example, screening should be performed on the condition that an absorption spectrum does not exist in the measurement results for the target drug that coincides with the absorption spectrum at a wave number of 1217.0 cm$^{-1}$ used as the index.

In addition, in the case of the target drug being, for example, an antibiotic effective against MRSA, screening should be performed on the condition that there is at least one coinciding absorption spectrum present in the spectral measurement results of the target drug among infrared absorption spectra used as indices at the above-mentioned wave numbers of 1076.2 cm$^{-1}$, 1195.8 cm$^{-1}$, 1234.4 cm$^{-1}$ and 1265.2 cm$^{-1}$ and so forth. Moreover, in the case of the target drug being, for example, an antibiotic effective against *Escherichia coli*, screening may be performed using as the index the infrared absorption spectrum at a wave number of 1259.4 cm$^{-1}$.

Moreover, in the case of the target drug being, for example, an anti-viral agent effective against KOS virus, screening should be performed on the condition that at least one coinciding absorption spectrum is present in the spectral measurement results of the target drug among infrared absorption spectra used as indices at the above-mentioned mentioned wave numbers of 1105.1 and 1122.5 cm$^{-1}$ and so forth.

Furthermore, the absorption spectra used as indices for an antibiotic effective against MRSA are not limited to those indicated above. The above values were merely confirmed as a result of measuring by using vancomycin as the sample, and there is a strong possibility that other absorption spectra exist that are characteristic of MRSA. An antibiotic more effective than vancomycin can be expected to be developed if other absorption spectra characteristic of MRSA can be identified. In addition, this applies similarly to an antibiotic effective against *Escherichia coli* and an anti-viral agent effective against KOS virus.

In addition, although the explanation here as well has focused on the use of FT-IR having a measuring accuracy of ±0.1 cm$^{-1}$, even in cases of more inferior measuring accuracy, it is still possible to perform drug screening. More specifically, a measuring accuracy of about ±1 cm$^{-1}$ should be obtained, and the above values to the right of the decimal point of wave numbers of the absorption spectra used as indices may be rounded up or down as is appropriate. Naturally, it is also possible to use FT-IR having superior measuring accuracy of ±0.1 cm$^{-1}$, and in this case, absorption spectra within the ranges included in the above values should be used as indices.

Thus, according to the drug screening method of the present embodiment, by using a simple method involving performing spectral analysis for a target drug, the target drug can be efficiently screened as to whether or not it is effective against cancer cells, bacteria or viruses, and by judging and processing spectral measurement results of a target drug using as indices the infrared absorption spectra corresponding to a plurality of wave numbers, this method is considered to be effective for primary screening and so forth in drug development in particular. As a result, both the time and cost required for drug development can be significantly reduced. Moreover, the present method is extremely effective in the case of eliminating adverse side effects from existing drugs. Namely, although the adverse side effects of a drug may be either inherent or not inherent to the drug's action, and it was difficult to find that difference with conventional drug development techniques, according to the present method, by identifying the energy spectrum specific to that adverse side effect in the manner of the myocardial toxicity previously described, it becomes easy to judge whether or not that adverse side effect is inherent to the action of the drug. Consequently, the time and cost required for developing drugs free of adverse side effects can be significantly reduced.

Next, an explanation is provided of an embodiment of the drug screening apparatus according to the present invention.

Figure 34:
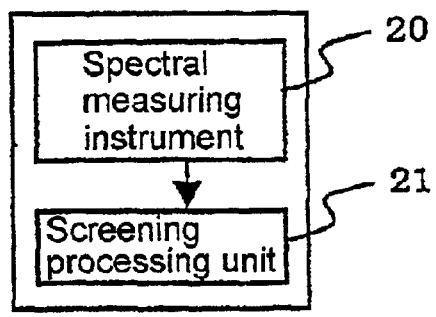
FIG. 34 is a block diagram showing the configuration of a drug screening apparatus as described in an embodiment of the present invention.

FIG. 34 is a block diagram showing the configuration of a drug screening apparatus as described in the present embodiment.

In FIG. 34, the present apparatus 2 is composed of spectral measuring instrument 20, which is used as spectral analysis means that performs analysis of absorption or emission spectra for a target drug, and a screening processing unit 21, which is used as screening means that screens a target drug based on the measurement results of the spectral measuring instrument 20. Here, an FT-IR system and so forth is used for the spectral measuring instrument 20 that measures absorption spectra for the infrared region. In addition, data relating to infrared absorption spectra used as indices for drug screening is preset in the screening processing unit 21.

In the screening apparatus 2 having the above configuration, infrared absorption spectrum is measured for a target drug by the spectral measuring instrument 20, and those measurement results are sent to the screening processing unit 21. In the screening processing unit 21, drug screening is performed using as indices the appearance of spectra corresponding to at least two wave numbers in the infrared region for the infrared absorption spectrum measured with the spectral measuring instrument 20 in the same manner as the above-mentioned step 202.

According to the present embodiment, a screening apparatus having a simple configuration can be realized that is able to efficiently screen target drugs.

In each of the above embodiments, although the explanations focused on the use of the infrared region as the specific region for performing analysis of energy spectra. It should be noted, however, that the present invention is not limited to use of the infrared region. Since the energy state of a cell system and so forth is expected to extend from the ultraviolet region to the microwave region in the form of molecular transitions, molecular vibrations and rotational energy, it is considered to be quite possible to apply the present invention to these regions as well.

In addition, although the case of measuring the absorption spectrum of a cell system and so forth has been indicated, attention may be focused on the emission spectrum of a system, and the present invention can also be applied in this case as well in the same manner as the case of the absorption spectrum.

Industrial Applicability

The present invention has considerable industrial applicability as a measuring and testing method for rapidly and reliably determining disease type and condition, and as the respective apparatuses for performing that measuring and testing. In addition, the present invention also has considerable industrial applicability as a method for rapidly and reliable screening various drugs, and as the respective apparatuses for performing that screening.

What is claimed is:

1. A method for determining at least one of disease type and condition which comprises analyzing an absorption or emission spectrum in a specific region for cells obtained from a specimen, and determining at least one of the disease type and condition by using as indices the appearance of spectra corresponding to at least two wave numbers, wherein said at least two wave numbers are obtained by measuring an absorption or emission spectrum of cancer cells, bacteria or virus within said specific region, which cells, bacteria or virus cause specific disease, and are wave numbers appearing or disappearing after death of the cells of the specimen, and said specific region includes the infrared region.

2. The method according to claim 1 that determines whether or not said specimen is cancer.

3. The method according to claim 2, wherein one of the wave numbers of the spectra used as said indices is 1261 $cm^{-1}$.

4. The method according to claim 2, wherein one of the at least two wave numbers of the spectra used as said indices is 1261.4 $cm^{-1}$.

5. The method according to claim 4, wherein another of the at least two wave numbers of the spectra used as said indices is at least one wave number substantially equal to that selected from the group consisting of 1163.1 $cm^{-1}$, 1168.8 $cm^{-1}$, 1203.6 $cm^{-1}$, 1211.3 $cm^{-1}$, 1224.7 $cm^{-1}$, 1257.5 $cm^{-1}$, 1290.3 $cm^{-1}$ and 1319.3 $cm^{-1}$.

6. The method according to claim 1 that determines whether or not said cells have specific bacteria.

7. The method according to claim 6, wherein said specific bacteria are drug resistance bacteria.

8. The method according to claim 7, wherein the drug resistance bacteria is methicillin-resistant *Staphylococcus aureus* and the at least two wave numbers of the spectra used as said indices are at least two wave numbers substantially equal to those selected from the group consisting of 1076.2 $cm^{-1}$, 1195.8 $cm^{-1}$, 1234.4 $cm^{-1}$ and 1265.2 $cm^{-1}$.

9. The method according to claim 1 that determines whether or not said cells are infected by a specific virus.

10. The method according to claim 9, wherein the virus is KOS virus and the at least two wave numbers of the spectra used as said indices are wave numbers substantially equal to 1105.1 $cm^{-1}$ and 1122.5 $cm^{-1}$.

11. The method according to claim 1, wherein said specimen includes cells infected with a virus and the at least two wave numbers appearing after death of the cells of the spectra used as said indices are wave numbers substantially equal to 1105.1 $cm^{-1}$ and 1122.5 $cm^{-1}$.

12. The method according to claim 1, wherein said specimen includes cells infected with a virus and the at least two wave numbers disappearing after death of the cells of the spectra used as said indices are at least two wave numbers substantially equal to those selected from the group consisting of 1037.6 $cm^{-1}$, 1055.0 $cm^{-1}$, 1068.5 $cm^{-1}$, 1103.2 $cm^{-1}$, 1209.3 $cm^{-1}$, 1232.4 $cm^{-1}$ and 1274.9 $cm^{-1}$.

13. An apparatus for diagnosing at least one of disease type and condition which comprises
spectral analysis means that analyzes an absorption or emission spectrum in a specific region for cells obtained from a specimen, and
diagnostic means that diagnoses at least one of disease type and condition using as indices the appearance of spectra corresponding to at least two wave numbers, wherein said at least two wave numbers are obtained by measuring an absorption or emission spectrum of cancer cells, bacteria or virus within said specific region, which cells, bacteria or virus cause specific disease, and are wave numbers appearing or disappearing after death of the cells of the specimen, and said specific region includes the infrared region.

14. The apparatus according to claim 13 that determines whether or not said specimen is cancer.

15. The apparatus according to claim 14 wherein one of the at least two wave numbers of the spectra used as said indices is 1261 $cm^{-1}$.

16. The apparatus according to claim 14, wherein one of the at least two wave numbers of the spectra used as said indices is 1261.4 $cm^{-1}$.

17. The apparatus according to claim 16, wherein another of the at least two wave numbers of the spectra used as said indices is at least one wave number substantially equal to that selected from the group consisting of 1163.1 cm$^{-1}$, 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$.

18. The apparatus according to claim 13 that determines whether or not said cells have specific bacteria.

19. The apparatus according to claim 18, wherein said specific bacteria are drug resistance bacteria.

20. The apparatus according to claim 19, wherein the drug resistance bacteria is methicillin-resistant *Staphylococcus aureus* and the at least two wave numbers of the spectra used as said indices are at least two wave numbers substantially equal to those selected from the group consisting of 1076.2 cm$^{-1}$, 1195.8 cm$^{-1}$, 1234.4 cm$^{-1}$ and 1265.2 cm$^{-1}$.

21. The apparatus according to claim 13 that determines whether or not said cells are infected by a specific virus.

22. The apparatus according to claim 21, wherein the virus is KOS virus and the at least two wave numbers of the spectra used as said indices are wave numbers substantially equal to 1105.1 cm$^{-1}$ and 1122.5 cm$^{-1}$.

23. A drug screening method comprising: analyzing an absorption or emission spectrum in a specific region for a target drug in combination with cells of a specimen, and screening said target drug by using as indices the appearance of spectra corresponding to at least two wave numbers, wherein said at least two wave numbers are obtained by measuring an absorption or emission spectrum of cancer cells, bacteria or virus within said specific region, which cells, bacteria or virus cause specific disease, and are wave numbers appearing or disappearing after death of the cells of the specimen, and said specific region includes the infrared region.

24. The drug screening method according to claim claim 23 wherein said target drug is an anti-cancer agent.

25. The drug screening method according to claim 24, wherein one of the at least two wave numbers of the spectra used as said indices is 1261 cm$^{-1}$ or 1163 cm$^{-1}$.

26. The drug screening method according to claim 25, wherein one of the at least two wave numbers of the spectra used as said indices is a wave number substantially equal to 1261.4 cm$^{-1}$ or 1163.1 cm$^{-1}$.

27. The drug screening method according to claim 26, wherein another of the at least two wave numbers of the spectra used as said indices is at least one wave number substantially equal to that selected from the group consisting of 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$.

28. The drug screening method according to claim 23; wherein said target drug is an antibiotic.

29. The drug screening method according to claim 28, wherein said antibiotic is effective against drug resistance bacteria.

30. The drug screening method according to claim 29, wherein the drug resistance bacteria is methicillin-resistant *Staphylococcus aureus* and the at least two wave numbers of the spectra used as said indices are at least two wave numbers substantially equal to those selected from the group consisting of 1076.2 cm$^{-1}$, 1195.8 cm$^{-1}$, 1234.4 cm$^{-1}$ and 1265.2 cm$^{-1}$.

31. The drug screening method according to claim 23, wherein said target drug is an anti-viral agent.

32. The drug screening method according to claim 31, wherein the anti-viral agent is active against KOS virus and the at least two wave numbers of the spectra used as said indices are wave numbers substantially equal to 1105.1 cm$^{-1}$ and 1122.5 cm$^{-1}$.

33. The drug screening method according to claim 23, wherein said specimen includes cells infected with a virus and the at least two wave numbers of the spectra used as said indices are wave numbers substantially equal to 1105.1 cm$^{-1}$ and 1122.5 cm$^{-1}$.

34. The drug screening method according to claim 23, wherein said specimen includes cells infected with a virus and the at least two wave numbers of the spectra used as said indices are at least two wave numbers substantially equal to those selected from the group consisting of 1037.6 cm$^{-1}$, 1055.0 cm$^{-1}$, 1068.5 cm$^{-1}$, 1103.2 cm$^{-1}$, 1209.3 cm$^{-1}$, 1232.4 cm$^{-1}$ and 1274.9 cm$^{-1}$.

35. A drug screening apparatus comprising:
spectral analysis means that analyzes the absorption or emission spectrum in a specific region for a target drug in combination with cells of a specimen, and
screening means that screens said target drug using as indices the appearance of spectra corresponding to at least two wave numbers, wherein said at least two wave numbers are obtained by measuring an absorption or emission spectrum of cancer cells, bacteria or virus within said specific region, which cells, bacteria or virus cause specific disease, and are wave numbers appearing or disappearing after death of the cells of the specimen, and said specific region includes the infrared region.

36. The apparatus according to claim 35 that determines whether or not said specimen is cancer.

37. The apparatus according to claim 35, wherein one of the at least two wave numbers of the spectra used as said indices is 1261 cm$^{-1}$.

38. The apparatus according to claim 36, wherein one of the at least two wave numbers of the spectra used as said indices is 1261.4 cm$^{-1}$.

39. The apparatus according to claim 38, wherein another of the at least two wave numbers of the spectra used as said indices is at least one wave number substantially equal to that selected from the group consisting of 1163.1 cm$^{-1}$, 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$.

40. The apparatus according to claim 35, that determines whether or not the cells of the specimen have specific bacteria.

41. The apparatus according to claim 40, wherein said specific bacteria are drug resistance bacteria.

42. The apparatus according to claim 41, wherein the drug resistance bacteria is methicillin-resistant *Staphylococcus aureus* and the at least two wave numbers of the spectra used as said indices are at least two wave numbers substantially equal to those selected from the group consisting of 1076.2 cm$^{-1}$, 1195.8 cm$^{-1}$, 1234.4 cm$^{-1}$ and 1265.2 cm$^{-1}$.

43. The apparatus according to claim 35 that determines whether or not the cells of the specimen are infected by a specific virus.

44. The apparatus according to claim 43, wherein the virus is KOS virus and the at least two wave numbers of the spectra used as said indices are wave numbers substantially equal to 1105.1 cm$^{-1}$ and 1122.5 cm$^{-1}$.

45. A method for determining at least one of disease type and condition which comprises analyzing an absorption or emission spectrum in a specific region for cells obtained from a specimen, and determining at least one of the disease type and condition by using as indices the appearance of spectra corresponding to at least two wave numbers, wherein said at least two wave numbers are obtained by measuring an absorption or emission spectrum of cancer cells within said specific region, wherein said specific region is an infrared region and one of the wave numbers is about 1261 cm$^{-1}$ and another of the at least two wave numbers is at least one wave number substantially equal to that selected from the group consisting of 1163.1 cm$^{-1}$, 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$, which are wave numbers appearing or disappearing after death of the cells of the specimen.

46. An apparatus for diagnosing at least one of disease type and condition which comprises spectral analysis means that analyzes an absorption or emission spectrum in a specific region for cells obtained from a specimen, and diagnostic means that diagnoses at least one of disease type and condition using as indices the appearance of spectra corresponding to at least two wave numbers, wherein said at least two wave numbers are obtained by measuring an absorption or emission spectrum of cancer cells within said specific region, wherein said specific region is an infrared region and one of the wave numbers is about 1261 cm$^{-1}$ and another of the at least two wave numbers is at least one wave number substantially equal to that selected from the group consisting of 1163.1 cm$^{-1}$, 1168.8 cm$^{-1}$, 1203.6 cm$^{-1}$, 1211.3 cm$^{-1}$, 1224.7 cm$^{-1}$, 1257.5 cm$^{-1}$, 1290.3 cm$^{-1}$ and 1319.3 cm$^{-1}$, which are wave numbers appearing or disappearing after death of the cells of the specimen.

47. A drug screening method comprising: analyzing an absorption or emission spectrum in a specific region for a target drug in combination with cells of a specimen, and screening said target drug by using as indices the appearance of spectra corresponding to at least two wave numbers, wherein said at least two wave numbers are obtained by measuring an absorption or emission spectrum of cancer cells, bacteria or virus within said specific region, which cells, bacteria or virus cause specific disease, and are wave numbers appearing or disappearing after death of the cells said of the specimen, said specific region is an infrared region, and the target drug is at least one selected from the group consisting of an anti-cancer agent, an antibiotic and an anti-viral agent.

48. A drug screening apparatus comprising:

spectral analysis means that analyzes the absorption or emissions spectrum in a specific region for a target drug in combination with cells of a specimen, and screening means that screens said target drug using as indices the appearance of spectra corresponding to at least two wave numbers, wherein said at least two wave numbers are obtained by measuring an absorption or emission spectrum of cancer cells bacteria or virus within said specific region, which cells, bacteria or virus cause specific disease, and are wave numbers appearing or disappearing after death of the cells of the specimen, said specific region is an infrared region, and the target drug is at least one selected from the group consisting of an anti-cancer agent, an antibiotic and an anti-viral agent.

* * * * *

UNITED STATES PATENT AND TRADEMARK OFFICE
CERTIFICATE OF CORRECTION

PATENT NO. : 6,743,637 B2
DATED : June 1, 2004
INVENTOR(S) : Tomoya Sato

It is certified that error appears in the above-identified patent and that said Letters Patent is hereby corrected as shown below:

Column 18,
Line 60, "claim 14 wherein" should read -- claim 14, wherein --.

Column 19,
Line 32, "to claim claim" should read -- to claim --.
Line 47, "claim 23;" should read -- claim 23, --

Column 20,
Line 27, "claim 35," should read -- claim 36, --.
Line 39, "claim 35, that" should read -- claim 35 that --.

Column 22,
Lines 6-7, "cells said of" should read -- cells of --.
Line 14, "emissions" should read -- emission --.
Line 20, "cells bacteria" should read -- cells, bacteria --.

Signed and Sealed this

Nineteenth Day of April, 2005

JON W. DUDAS
*Director of the United States Patent and Trademark Office*